United States Patent [19]

Kon et al.

[11] Patent Number: 4,870,074
[45] Date of Patent: Sep. 26, 1989

[54] SUBSTITUTED BENZAMIDE DERIVATIVES, FOR ENHANCING GASTROINTESTINAL MOTILITY

[75] Inventors: Tatsuya Kon, Ashiya; Shiro Kato, Sakai; Toshiya Morie, Matsubara; Kazunori Ohno, Higashi-Osaka; Katsuhiko Hino, Ikoma; Tadahiko Karasawa, Toyonaka; Naoyuki Yoshida, Matsubara, all of Japan

[73] Assignee: Dainippon Pharmaceutical Co., Ltd., Japan

[21] Appl. No.: 42,474

[22] Filed: Apr. 24, 1987

[30] Foreign Application Priority Data

Apr. 30, 1986 [JP] Japan ............................ 61-101552
Dec. 31, 1986 [JP] Japan ............................ 61-315090

[51] Int. Cl.⁴ .................. C07D 265/30; C07D 413/12; A61K 31/535
[52] U.S. Cl. .............................. 514/233.8; 514/237.8; 544/169; 544/148; 544/131; 544/137; 544/146; 544/152
[58] Field of Search ................... 544/169, 148; 514/237.8, 233.8

[56] References Cited

U.S. PATENT DOCUMENTS

| | | | |
|---|---|---|---|
| 3,502,652 | 3/1970 | Jacker et al. | 544/169 |
| 4,029,786 | 6/1977 | Young | 514/237.8 |
| 4,210,754 | 7/1980 | Burkard et al. | 544/169 |
| 4,323,503 | 4/1982 | Thominet et al. | 544/148 |
| 4,605,654 | 8/1986 | Cousse et al. | 544/148 |
| 4,692,445 | 9/1987 | Kahla et al. | 514/233.8 |

FOREIGN PATENT DOCUMENTS

| | | | |
|---|---|---|---|
| 3090274 | 8/1978 | Japan | 544/169 |
| 1184396 | 3/1970 | Switzerland | 544/148 |

OTHER PUBLICATIONS

CA:23071W Tahara et al, Morpholine derivatives, 8/8/78, 4 pp.

CA:108:94575q Tatsuya et al, Prep. of N-(2-morpholinyl alkyl) bezamides and analogs, 11/4/87, 95 pp.

Primary Examiner—Richard A. Schwartz
Assistant Examiner—John A. H. Russell
Attorney, Agent, or Firm—Scully, Scott, Murphy & Presser

[57] ABSTRACT

Compounds of the formula:

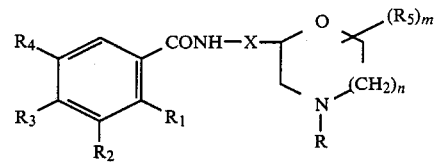

wherein R is hydrogen, alkoxycarbonyl, benzyloxycarbonyl, heteroarylalkyl, phenylalkenyl, or —T—(Y)$_p$—R$_6$ (wherein T is single bond or alkylene, Y is oxygen, sulfur or carbonyl, R$_6$ is phenyl, substituted phenyl, naphthyl, or diphenylmethyl, and p is 0 or 1, provided that when T is single bond, p is 0); R$_1$ is halogen, hydroxy, alkoxy, cycloalkyloxy, alkenyloxy, alkynyloxy, alkoxy interrupted by oxygen or carbonyl, alkylthio, amino, monosubstituted amino, or a substituted alkoxy; R$_2$ is hydrogen; R$_3$ is hydrogen, halogen, amino, alkylamino, dialkylamino, alkanoylamino, or nitro; R$_4$ is hydrogen, halogen, nitro, sulfamoyl, alkylsulfamoyl, or dialkylsulfamoyl; or any two adjacent groups of the R$_1$, R$_2$, R$_3$ and R$_4$ may combine to form alkylenedioxy, and the remaining two groups are each hydrogen; R$_5$ is hydrogen or alkyl; X is alkylene; m and n are each 1 or 2; provided that at least one of the groups R$_2$, R$_3$ and R$_4$ is other than hydrogen, and acid addition salts, quaternary ammonium salts and N-oxide derivatives thereof, processes for preparation thereof, and pharmaceutical composition containing the same. Said compounds, salts and N-oxide derivatives thereof show excellent gastrointestinal motility enhancing activity.

28 Claims, No Drawings

SUBSTITUTED BENZAMIDE DERIVATIVES, FOR ENHANCING GASTROINTESTINAL MOTILITY

This invention relates to novel substituted benzamide derivatives having a gastrointestinal motility enhancing activity, processes for the preparation thereof, and a method of using the same, and pharmaceutical compositions containing said compound as an active ingredient.

PRIOR ART

It is disclosed in Japanese Patent Publication (unexamined) No. 90274/1978 [Chem. Abstr., 90, 23071W (1970)] that certain N-[(4-lower alkyl-2(or 3)-morpholinyl)methyl]benzamide derivatives have antireserpine activity, analgesic activity, etc. and are useful, for example, as antidepressants or analgesics.

On the other hand, various benzamide derivatives have been synthesized and pharmacological properties thereof have been investigated since the mid-1960's, when 4-amino-5-chloro-N-[(2-diethylamino)ethyl]-2-methoxybenzamide [generic name: metoclopramide, cf. Merck Index, 10th Ed., 6019 (1983)] has been developed as an antiemetic agent or gastrointestinal motility enhancing agent. However, there is not yet found any substituted benzamide derivative having superior activity to that of metoclopramide as a gastrointestinal motility enhancing agent.

SUMMARY DESCRIPTION OF THE INVENTION

The present inventors have extensively studied in order to obtain novel substituted benzamide derivatives having excellent gastrointestinal motility enhancing activity and have found that certain substituted benzamide derivatives wherein the nitrogen atom in the amide moiety is bound with the carbon atom at 2-position of morpholine or hexahydro-1,4-oxazepine group via an alkylene group show the desired activity and further that some of these substituted benzamide derivatives show more potent gastrointestinal motility enhancing activity but show less adverse effects on the central nervous system than those of metoclopramide.

An object of the invention is to provide novel substituted benzamide derivatives having excellent gastrointestinal motility enhancing activity. Another object of the invention is to provide processes for the preparation of the compounds. A further object of the invention is to provide a pharmaceutical composition containing as an active ingredient the compounds as set forth above which is useful as a gastrointestinal motility enhancing agent. These and other objects and advantages of the invention will be apparent to skilled persons in this field from the following description.

DETAILED DESCRIPTION OF THE INVENTION

The substituted benzamide derivatives of this invention are compounds of the formula:

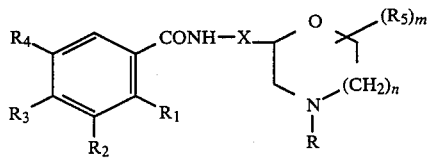

wherein R is hydrogen, a $C_2$–$C_5$ alkoxycarbonyl, benzyloxycarbonyl, a heteroaryl($C_1$–$C_3$)alkyl in which the heteroaryl is furyl, thienyl, pyridyl, or 1,2-benzisoxazolyl, a phenyl($C_3$–$C_5$)alkenyl, or —T—$(Y)_p$—$R_6$ (wherein T is a single bond or a $C_1$–$C_6$ alkylene, Y is oxygen, sulfur or carbonyl, $R_6$ is phenyl, a phenyl substituted by one to five members each independently selected from the group consisting of a halogen, a $C_1$–$C_4$ alkyl, trifluoromethyl, a $C_1$–$C_4$ alkoxy, nitro, cyano and amino, naphthyl, or diphenylmethyl, and p is 0 or 1, provided that when T is a single bond, p is 0), $R_1$ is a halogen, hydroxy, a $C_1$–$C_{12}$ alkoxy, a $C_3$–$C_6$ cycloalkyloxy, a $C_3$–$C_8$ alkenyloxy, a $C_3$–$C_8$ alkynyloxy, a $C_2$–$C_6$ alkoxy interrupted by one or two oxygens or carbonyls, a $C_1$–$C_4$ alkylthio, amino, a monosubstituted amino in which the substituted is a $C_1$–$C_8$ alkyl, a phenyl($C_1$–$C_3$)alkyl or a $C_3$–$C_6$ cycloalkyl, a $C_2$–$C_6$ alkoxy in which the carbon atom at any position other than the 1-position is substituted by one hydroxy or amino, or a substituted $C_1$–$C_6$ alkoxy in which the substituent is a halogen, cyano, a $C_2$–$C_5$ alkoxycarbonyl, phthalimido, a $C_3$–$C_6$ cycloalkyl, a phenyl optionally substituted by one halogen, a phenoxy optionally substituted by one halogen, or a benzoyl optionally substituted by one halogen, $R_2$ is hydrogen, $R_3$ is hydrogen, a halogen, amino, a $C_1$–$C_4$ alkylamino, a di($C_1$–$C_4$ alkyl)amino, a $C_2$–$C_5$ alkanoylamino, or nitro, $R_4$ is hydrogen, a halogen, nitro, sulfamoyl, a $C_1$–$C_4$ alkylsulfamoyl, or a di($C_1$–$C_4$ alkyl)sulfamoyl, or any two adjacent groups of the $R_1$, $R_2$, $R_3$ and $R_4$ combine to form a $C_1$–$C_3$ alkylenedioxy, and the remaining two groups are each hydrogen, $R_5$ is hydrogen or a $C_1$–$C_4$ alkyl, X is a $C_1$–$C_3$ alkylene, and m and n are each 1 or 2, provided that at least one of the groups $R_2$, $R_3$ and $R_4$ is not hydrogen, and pharmaceutically acceptable acid addition salts, quaternary ammonium salts and N-oxide derivatives thereof.

The pharmaceutically acceptable acid addition salts of the compounds (I) include, for example, inorganic acid addition salts (e.g. hydrochloride, hydrobromide, hydroiodide, sulfate, phosphate, etc.) and organic acid addition salts (e.g. oxalate, maleate, fumarate, lactate, malate, citrate, tartrate, benzoate, methanesulfonate, etc.).

The pharmaceutically acceptable quaternary ammonium salts of the compounds (I) mean pharmaceutically acceptable ammonium salts of the compounds of the formula (I) wherein R is other than hydrogen, alkoxycarbonyl or benzyloxycarbonyl and include, for example, quaternary ammonium salts with lower alkyl halogenides (e.g. methyl iodide, methyl bromide, ethyl iodide, ethyl bromide, etc.), lower alkyl lower alkylsulfonates (e.g. methyl methanesulfonate, ethyl methanesulfonate, etc.), lower alkyl arylsulfonates (e.g. methyl ptoluenesulfonate, etc.), or the like.

The N-oxide derivatives of the compounds (I) mean N-oxide derivatives on the morpholine or hexahydro-1,4-oxazepine moiety of the compounds of the formula (I) wherein R is other than hydrogen, alkoxycarbonyl, benzyloxycarbonyl, thienylalkyl, pyridylalkyl, and —T′—S—$R_6$ ($R_6$ is as defined above and T′ is an alkylene), and $R_1$ is other than alkylthio.

The compounds (I), acid addition salts, quaternary ammonium salts and N-oxide derivatives thereof may optionally be present in the form of a hydrate or solvate, and the hydrate and solvate are also included in this invention.

The compounds of the formula (I) contain one or more asymmetric carbon atoms, and hence, they may be present in the form of various stereoisomers. This invention includes also these stereoisomers and a mixture thereof and racemic compounds.

The terms for the atom or groups used in the present specification have the following meanings.

The alkyl group, alkyl moiety, alkylene group, or alkylene moiety includes straight or branched chain groups. The "alkoxycarbonyl" includes, for example, methoxycarbonyl, ethoxycarbonyl, propoxycarbonyl, and the like. The "alkylene" includes, for example, methylene, ethylene, methylmethylene, trimethylene, propylene, dimethylmethylene, tetramethylene, pentamethylene, hexamethylene, and the like. The "halogen" includes fluorine, chlorine, bromine, and iodine, preferably fluorine, chlorine, and bromine. The "alkyl" includes, for example, methyl, ethyl, propyl, isopropyl, butyl, pentyl, hexyl, and the like. The "alkoxy" includes, for example, methoxy, ethoxy, propoxy, isopropoxy, butoxy, isobutoxy, sec-butoxy, pentyloxy, isopentyloxy, hexyloxy, isohexyloxy, heptyloxy, octyloxy, nonyloxy, decyloxy, undecyloxy, dodecyloxy, and the like. The "cycloalkyl" includes, for example, cyclopropyl, cyclobutyl, cyclopentyl, cyclohexyl, and the like. The "alkenyloxy" means a group which has one double bond at the position other than the carbon atom adjacent to the oxygen atom, and includes, for example, allyloxy, 2-butenyloxy, 3-butenyloxy, 3-methyl-2-butenyloxy, 3- or 4-pentenyloxy, 4- or 5-hexenyloxy, 6-heptenyloxy, and the like. The "alkynyloxy" means a group which has one triple bond at the position other than the carbon atom adjacent to the oxygen atom, and includes, for example, 2-propynyloxy, 3-butynyloxy, 5-hexynyloxy, and the like. The "alkoxy interrupted by one or two oxygens or carbonyls" includes, for example, 2-methoxyethoxy, (2-methoxyethoxy)methoxy, 2,2-dimethoxyethoxy, 2-oxopropoxy, 3-oxobutoxy, and the like. The "alkanoylamino" includes, for example, acetylamino, propionylamino, butyrylamino, isobutyrylamino, and the like.

Among the compounds of this invention, preferred ones are compounds of the formula (I) wherein R is pyridylmethyl,

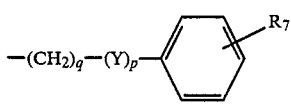

(wherein Y and p are as defined above, $R_7$ is hydrogen, fluorine, chlorine, trifluoromethyl, cyano, or nitro, and q is an integer of 1 to 4), pentafluorobenzyl, 2-nitro-4-chlorobenzyl, 1-phenylethyl, or naphthylmethyl; $R_1$ is hydroxy, a $C_1$–$C_{10}$ alkoxy, a $C_5$–$C_6$ cycloalkyloxy, a $C_3$–$C_5$ alkenyloxy, a $C_3$–$C_5$ alkynyloxy, a $C_2$–$C_4$ alkoxy interrupted by one carbonyl, a $C_2$–$C_5$ alkoxy in which the carbon atom at any position other than the 1-position is substituted by one hydroxy, or a substituted $C_1$–$C_5$ alkoxy in which the substituent is a halogen, cyano, a $C_2$–$C_4$ alkoxycarbonyl, a $C_3$–$C_5$ cycloalkyl, a phenyl optionally substituted by one halogen, a phenoxy optionally substituted by one halogen, or a benzoyl optionally substituted by one halogen; $R_2$ is hydrogen; $R_3$ is amino, a di($C_1$–$C_2$ alkyl)amino or a $C_2$–$C_5$ alkanoylamino; $R_4$ is chlorine; $R_5$ is hydrogen or methyl; X is methylene or ethylene; m is 1; and n is 1 or 2, and pharmaceutically acceptable acid addition salts, quaternary ammonium salts and N-oxide derivatives thereof.

More preferred compounds are compounds of the formula:

TABLE 1

| GLUCOAMYLASE ACTIVITY SECRETED BY THE TRANSFORMED YEAST STRAINS | |
|---|---|
| TRANSFORMANT | GLUCOAMYLASE ACTIVITY[a] COMPLETE MEDIA |
| YEp(DEX)3 | 33.4 |
| YEp(DEX)4 | 61.9 |
| YEp(DEX)5 | 25.3 |
| YEp(DEX)6 | 47.7 |
| YEp(DEX)7 | 17.8 |
| YEp(DEX)9 | 33.3 |
| S. cerevisiae LL20 | 4.9 |
| S. diastaticus (J3120-13C) | 1449.7 |

[a]Glucoamylase activity is expressed as the amount of glucose (μg/ml) hydrolyzed from 2% dextrin at 25° C. in 1 h, in a cell free system.

wherein
$R_a$ is pyridylmethyl, benzyl, fluorobenzyl, chlorobenzyl, trifluoromethylbenzyl, cyanobenzyl, or 3-(4-chlorophenoxy)propyl, $R_{1a}$ is a $C_1$–$C_7$ alkoxy, cyclopentyloxy, 3-butenyloxy, 3-methyl-2-butenyloxy, 2-oxopropoxy, 2-hydroxypropoxy, or 2-chloroethoxy, $R_3'$ is amino, dimethylamino or a $C_2$–$C_3$ alkanoylamino, $R_5'$ is hydrogen or methyl, and n is 1 or 2, and pharmaceutically acceptable acid addition salts, quaternary ammonium salts and N-oxide derivatives thereof.

Particularly preferred compounds are compounds of the formula:

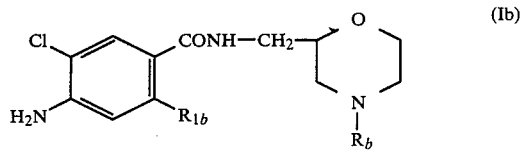

(Ib)

wherein
$R_b$ is pyridylmethyl, benzyl, fluorobenzyl, chlorobenzyl, or 3-(4-chlorophenoxy)propyl, and $R_{1b}$ is methoxy, ethoxy, butoxy, isobutoxy, pentyloxy, isopentyloxy, 3-methyl-2-butenyloxy, or 2-hydroxypropoxy, and pharmaceutically acceptable acid addition salts and N-oxide derivatives thereof.

Specific examples of the particularly preferred compounds are the following compounds and pharmaceutically acceptable acid addition salts thereof:

4-amino-5-chloro-2-ethoxy-N-[[4-(4-fluorobenzyl)-2-morpholinyl]methyl]benzamide, 4-amino-5-chloro-2-ethoxy-N-[[4-(3-pyridyl)methyl-2-morpholinyl]methyl]benzamide, 4-amino-N-[(4-benzyl-2-morpholinyl)methyl]-5-chloro-2-(3-methyl-2-butenyloxy)benzamide, 4-amino-N-[(4-benzyl-2-morpholinyl)methyl]-2-butoxy-5-chlorobenzamide, 4-amino-2-butoxy-5-chloro-N-[[4-(4-fluorobenzyl)-2-morpholinyl]methyl]benzamide, 4-amino-N-[(4-benzyl-2-morpholinyl)methyl]-5-chloro-2-isopentyloxybenzamide, 4-amino-5-chloro-N-[[4-(2-chlorobenzyl)-2-morpholinyl]methyl]-2-ethoxybenzamide, 4-amino-N-[(4-benzyl-2-morpholinyl)methyl]-5-chloro-2-ethoxybenzamide, 4-amino-N-[(4-benzyl-2-morpholinyl)methyl]-5-chloro-2-methoxybenzamide, 4-amino-5-chloro-N-[[4-(4-cyanobenzyl)-2-morpholinyl]methyl]-2-methoxybenzamide, and 4-amino-5-chloro-N-[[4-[3-(4-chlorophenoxy)propyl]-2-morpholinyl]methyl]-2-methoxybenzamide.

The compounds of this invention can be prepared by various processes, for example, by the following processes.

Process (a):

The compounds of the formula (I) can be prepared by reacting a compound of the formula:

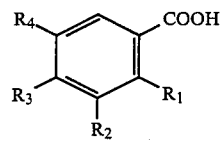

wherein $R_1$, $R_2$, $R_3$ and $R_4$ are as defined above, or a reactive derivative thereof with a compound of the formula:

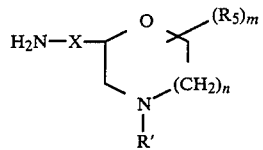

wherein $R_5$, X, m and n are as defined above, and R' is the same as R except hydrogen, and when a compound of the formula (I) wherein R is a $C_2$-$C_5$ alkoxycarbonyl, benzyloxycarbonyl or benzyl is obtained, optionally removing the said group from the group.

The reactive derivative of the compound (II) includes, for example, activated esters, acid anhydrides, acid halides (particularly acid chloride) and lower alkyl esters. Suitable examples of the activated esters are p-nitrophenyl ester, 2,4,5-trichlorophenyl ester, pentachlorophenyl ester, cyanomethyl ester, N-hydroxysuccinimide ester, N-hydroxyphthalimide ester, 1-hydroxybenzotriazole ester, N-hydroxy-5-norbornene-2,3-dicarboximide ester, N-hydroxypiperidine ester, 8-hydroxyquinoline ester, 2-hydroxyphenyl ester, 2-hydroxy-4,5-dichlorophenyl ester, 2-hydroxypyridine ester, 2-pyridylthiol ester, and the like. The acid anhydrides include symmetric acid anhydrides and mixed acid anhydrides. Suitable examples of the mixed acid anhydrides are mixed acid anhydrides with alkyl chloroformates (e.g. ethyl chloroformate, isobutyl chloroformate, etc.), mixed acid anhydrides with aralkyl chloroformates (e.g. benzyl chloroformate, etc.), mixed acid anhydrides with aryl chloroformates (e.g. phenyl chloroformate, etc.), mixed acid anhydrides with alkanoic acids (e.g. isovaleric acid, pivalic acid, etc.), and the like.

When the compounds (II) are used, the reaction can be carried out in the presence of a condensation agent, such as dicyclohexylcarbodiimide, 1-ethyl-3-(3-dimethylaminopropyl)carbodiimide hydrochloride, N,N'-carbonyldiimidazole, 1-ethoxycarbonyl-2-ethoxy-1,2-dihydroquinoline, and the like. When dicyclohexylcarbodiimide or 1-ethyl-3-(3-dimethylaminopropyl)carbodiimide hydrochloride is used as the condensation agent, such reagents as N-hydroxysuccinimde, 1-hydroxybenzotriazole, 3-hydroxy-4-oxo-3,4-dihydro-12,3-benzotriazine, or N-hydroxy-5-norbornene-2,3-dicarboximide may be added to the reaction system.

The reaction of the compound (II) or a reactive derivative thereof and the compound (III) is carried out in a suitable solvent or without using any solvent. Suitable solvent is selected in accordance with the kinds of the starting compounds, and includes, for example, aromatic hydrocarbons (e.g. benzene, toluene, xylene, etc.), ethers (e.g. diethyl ether, diisopropyl ether, tetrahydrofuran, dioxane, etc.), halogenated hydrocarbons (e.g. dichloromethane, chloroform, etc.), ethyl acetate, acetonitrile, dimethylformamide, dimethyl sulfoxide, ethylene glycol, water, and the like. These solvents may be used alone or in combinaion of two or more thereof. When the acid is liberated during the course of the reaction, the reaction may optionally be carried out in the presence of a base. Suitable examples of the base are alkali metal bicarbonates (e.g. sodium bicarbonate, potassium bicarbonate, etc.), alkali metal carbonates (e.g. sodium carbonate, potassium carbonate, etc.), and organic bases (e.g. triethylamine, tributylamine, diisopropylethylamine, N-methylmorpholine, etc.). The compound (III) may be used in an excess amount to serve as the base. The reaction temperature may vary in accordance with the kinds of the starting compounds, but is usually in the range of from about $-30°$ C. to about 200° C., preferably from about $-10°$ C. to about 150° C., and the reaction period of time is usually in the range of from 1 hour to 48 hours.

When the compound (II) has such a functional group which interferes with the reaction as an aliphatic amino, it is preferable to block previously the group with an appropriate protecting group such as a lower alkanoyl (e.g. acetyl). The protecting group can be removed after the reaction.

When a compound of the formula (I) wherein R is a $C_2$-$C_5$ alkoxycarbonyl, benzyloxycarbonyl, or benzyl is obtained by the above process (a), the group is removed to give a compound of the formula (I) wherein R is hydrogen. The removal of these groups can be carried out by a conventional method. For instance, in case of R being an alkoxycarbonyl, the product is subjected to hydrolysis under an alkaline condition, and in case of R being benzyloxycarbonyl or benzyl, the product is subjected to hydrogenolysis. The hydrolysis under an alkaline condition is carried out by using a base in an appropriate solvent. The solvent includes, for example, alcohols (e.g. methanol, ethanol, isopropyl alcohol, etc.), dioxane, water, or a mixture thereof. The base includes, for example, alkali metal hydroxides (e.g. sodium hydroxide, potassium hydroxide, etc.). The hydrolysis is usually carried out at a temperature of from about 50° C. to about 100° C. for 0.5 to 24 hours. The hydrogenolysis can be carried out in an appropriate solvent in the presence of a catalyst. The solvent includes, for example, alcohols (e.g. methanol, ethanol, isopropyl alcohol, etc.), ethyl acetate, acetic acid, dioxane, water, or a mixture thereof. The catalyst includes, for example, palladium on carbon, and the like. The hydrogenolysis is usually carried out at a temperature of from 20° C. to about 80° C. for 1 to 24 hours.

When a compound of the formula (I) wherein $R_3$ is a $C_2$-$C_5$ alkanoylamino is obtained in the above process (a), the product may further be subjected to hydrolysis under an acidic or alkaline condition to give a compound of the formula (I) wherein $R_3$ is amino. The alkanoyl group can easily be removed. For instance, when a lower alkyl ester of compound (II) wherein $R_3$ is an alkanoylamino is reacted with a compound (III) at 120°–150° C., there can be obtained a compound of the formula (I) wherein R is amino.

Many of the starting compounds (II) are known, and can easily be prepared by the methods as disclosed in literatures, for example, French Pat. No. 1,307,995, U.S. Pat. Nos. 3,177,252, 3,342,826 and 3,892,802, G.B. Pat. No. 1,153,796, European Pat. Nos. 76,530 and 102,195, and J. Chem. Soc., 1963, 4666. Novel compounds (II) can also be prepared by these known methods or by the methods as disclosed in Reference Examples 80, 81 and 83 to 87 hereinafter.

The starting compounds (III) are novel and can be prepared, for example, by the methods as disclosed in Reference Examples 1, 3 to 6, 56, 58, 60 to 76, and 79 hereinafter.

Process (b):

The compounds of the formula:

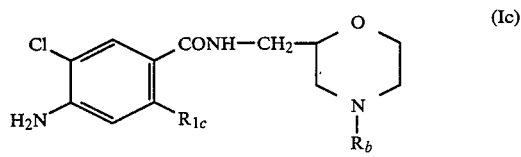

wherein $R_b$ is as defined above, and $R_{1c}$ is methoxy, ethoxy, butoxy, isobutoxy, pentyloxy, or isopentyloxy, can be prepared by chlorinating a compound of the formula:

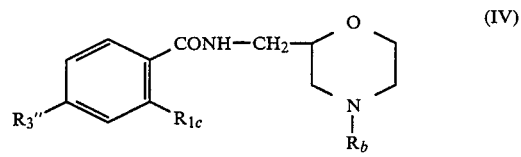

wherein $R_b$ and $R_{1c}$ are as defined above, and $R_3''$ is a $C_2$-$C_5$ alkanoylamino, followed by removing the alkanoyl group from the product.

The first chlorination step can be carried out by a known method, for example, by reacting the compound (IV) with a chlorinating agent in an appropriate solvent. The chlorinating agent includes, for example, N-chlorosuccinimide, iodobenzene dichloride, t-butyl hypochlorite, and the like. The solvent may vary depending on the kinds of the chlorinating agent and the like, and includes, for example, halogenated hydrocarbons (e.g. dichloromethane, chloroform, 1,2-dichloroethane, etc.), ethers (e.g. tetrahydrofuran, etc.), acetonitrile, dimethylformamide, pyridine, and the like. The reaction temperature may vary depending on the kinds of the chlorinating agent, and the like, but is usually in the range of from about −20° C. to about 100° C., and the reaction period of time is usually in the range of from 1 hour to 24 hours.

The removal of the alkanoyl group from the chlorinated product is effected by hydrolysis or by treatment with an organic amine. The hydrolysis is carried out in an appropriate solvent under an acidic or alkaline condition. The solvent includes, for example, alcohols (e.g. methanol, ethanol, isopropyl alcohol, etc.), dioxane, water, or a mixture thereof. The acid includes mineral acids (e.g. hydrochloric acid, etc.), and the base includes alkali metal hydroxides (e.g. sodium hydroxide, potassium hydroxide, etc.), alkali metal carbonates (e.g. sodium carbonate, potassium carbonate, etc.), and the like. The treatment of the chlorinated product with an organic amine is carried out in the absence or presence of a solvent. The solvent includes, for example, aromatic hydrocarbons (e.g. benzene, toluene, etc.), ethers (e.g. tetrahydrofuran, dioxane, etc.), halogenated hydrocarbons (e.g. dichloromethane, chloroform, etc.), alcohols (e.g. methanol, ethanol, isopropyl alcohol, etc.), ethyl acetate, acetonitrile, and the like. The organic amine includes, for example, lower alkylamines (e.g. methylamine, ethylamine, etc.), di(lower alkyl)amines (e.g. dimethylamine, diethylamine, etc.), and the like. The removal of the alkanoyl group is usually carried out at a temperature of from about 20° C. to about 100° C. for 0.5 to 8 hours.

The starting compound (IV) can be prepared, for example, by reacting an appropriate 4-alkanoylamino-2-alkoxybenzoic acid or a reactive derivative thereof with an appropriate 2-aminomethyl-4-substituted morpholine in the same manner as in the above process (a).

Process (c):

The compound (Ic) can also be prepared by reducing a compound of the formula:

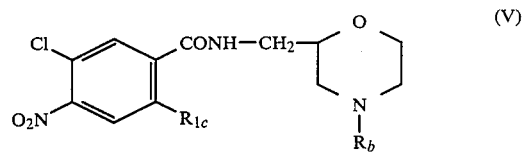

wherein $R_b$ and $R_{1c}$ are as defined above.

The above reduction can be carried out by a conventional process, for example, by treating the compound (V) with a reducing agent in an appropriate solvent. The reducing agent includes a combination of a metal (e.g. tin, zinc, iron, etc.) or a metal salt (e.g. stannous chloride, etc.) and an acid (e.g. hydrochloric acid, acetic acid, etc.), and the like. Stannous chloride may be used alone as the reducing agent. Alternatively, the reduction can also be carried out by hydrogenating the compound (V) in the presence of a catalyst in a solvent. Suitable examples of the catalyst are palladium on carbon, and the like. A suitable solvent is selected in accordance with the kinds of the reducing agent or means, and includes, for example, alcohols (e.g. methanol, ethanol, isopropyl alcohol, etc.), ethyl acetate, acetic acid, dioxane, water, or a mixture thereof.

The reaction temperature may vary depending on the kinds of the reducing agent or means, but is usually in the range of from about 10° C. to about 100° C., and for catalytic hydrogenation, preferably from about 10° C. to about 50° C. The reaction period of time is usually in the range of from 1 hour to 24 hours.

The starting compound (V) can be prepared, for example, by reacting an appropriate 2-alkoxy-5-chloro-4-nitrobenzoic acid or a reactive derivative thereof with an appropriate 2-aminomethyl-4-substituted morpholine in the same manner as in the above process (a). The 2-alkoxy-5-chloro-4-nitrobenzoic acid can be prepared, for example, by the process disclosed in G.B. Patent No. 1,153,796.

Process (d):

The compound (Ic) can also be prepared by reacting a compound of the formula:

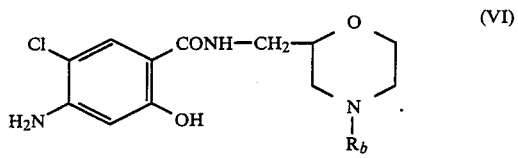

wherein $R_b$ is as defined above, with a compound of the formula:

$$Z-R_8 \qquad (VII)$$

wherein $R_8$ is methyl, ethyl, butyl, isobutyl, pentyl, or isopentyl, and Z is a residue of a reactive ester of an alcohol.

In the formula (VII) the residue of reactive ester of an alcohol as defined for Z includes, for example, a halogen atom (e.g. chlorine, bromine or iodine), a lower alkylsulfonyloxy (e.g. methanesulfonyloxy, ethanesulfonyloxy, etc.), an arylsulfonyloxy (e.g. benzenesulfonyloxy, p-toluenesulfonyloxy, m-nitrobenzenesulfonyloxy, etc.), a lower alkoxysulfonyloxy (e.g. methoxysulfonyloxy, ethoxysulfonyloxy, etc.), and the like.

The above reaction is usually carried out in an appropriate solvent in the presence of a base. Suitable examples of the base are alkali metal carbonates (e.g. sodium carbonate, potassium carbonate, etc.), quaternary ammonium hydroxides (e.g. tetrabutylammonium hydroxide, benzyltriethylammonium hydroxide, etc.), alkali metal alkoxides (e.g. sodium methoxide, sodium ethoxide, etc.), alkali metal hydrides (e.g. sodium hydride, potassium hydride, etc.), and the like. A suitable solvent may be selected in accordance with the kinds of the starting compound, base, and the like, and includes, for example, dichloromethane, acetone, acetonitrile, methanol, ethanol, isopropyl, alcohol, diglyme, dimethylformamide, dimethylacetamide, and the like. When the compound of the formula (VII) wherein Z is chlorine or bromine is used, the reaction can proceed more smoothly by adding an alkali metal iodide (e.g. sodium iodide, potassium iodide, etc.) to the reaction system.

Alternatively, the above reaction can also be carried out in the presence of a strong base (e.g. sodium hydroxide, potassium hydroxide, etc.) and a phase transfer catalyst in a phase transfer solvent system such as dichloromethane-water. Suitable examples of the phase transfer catalyst are tetrabutylammonium bromide, cetyltrimethylammonium bromide, benzyltriethylammonium chloride, tetrabutylammonium bisulfate, and the like.

The reaction temperature may vary depending on the kinds of the starting compound, and the like, but is usually in the range of from about 5° C. to 150° C., and the reaction period of time is usually in the range of 5 to 48 hours.

The starting compound (VI) can be prepared, for example, by reacting 2-acetoxy-4-acetylamino-5-chlorobenzoic acid or a reactive derivative thereof with an appropriate 2-aminomethyl-4-substituted morpholine in the same manner as in the above process (a), followed by hydrolysis of the resulting product. The compound (VI) can also be prepared by demethylating the corresponding 2-methoxy compound with sodium ethanethiolate in dimethylformamide or with boron tribromide in dichloromethane.

The compounds (I) prepared by the above processes can be isolated and purified by conventional techniques, such as chromatography, recrystallization of reprecipitation.

The compounds (I) may be obtained in the form of a free base, acid addition salts, hydrate or solvate depending on the kinds of the starting compounds, the reaction and treating conditions, and the like. The acid addition salt can be converted into a free base by treating it with a base such as an alkali metal hydroxide or an alkali metal carbonate in the usual manner. On the other hand, the free base may be converted into an acid addition salt by treating it with various acids in the usual manner. For example, when a compound of the formula (I) is reacted with an appropriate acid in a solvent and the reaction product is purified by recrystallization or reprecipitation, there is obtained an acid addition salt of the compound (I). The solvent includes, for example, chloroform, acetone, methanol, ethanol, isopropyl alcohol, water, or a mixture thereof. The reaction temperature is usually in the range of from about 0° C. to about 80° C., and the reaction period of time is usually in the range of from 30 minutes to 48 hours.

The compounds of the formula (I) in which R is other than hydrogen, alkoxycarbonyl or benzyloxycarbonyl may be converted into their quaternary ammonium salts in the usual manner. The quaternization is carried out by reacting the compound (I) with an appropriate quaternizing agent in the absence or presence of a solvent. The solvent includes, for example, aromatic hydrocarbons (e.g. benzene, toluene, xylene, etc.), ketones (e.g. acetone, methyl ethyl ketone, methyl isobutyl ketone, etc.), acetonitrile, or a mixture thereof. The reaction temperature may vary depending on the kinds of the compound (I) and the quaternizing agent, but is usually in the range of about 10° C. to 130° C., and the reaction period of time is usually in the range of 1 to 72 hours.

The compounds of the formula (I) in which R is other than hydrogen, alkoxycarbonyl, benzyloxycarbonyl, thienylalkyl, pyridylalkyl, or —T'—S—$R_6$ wherein $R_6$ and T' are as defined above may be converted into their N-oxide derivatives in the usual manner. The N-oxidation is carried out by reacting the compound (I) with an appropriate oxidizing agent in a solvent. The oxidizing agent includes, for example, hydrogen peroxide and organic peracids (e.g. peracetic acid, perbenzoic acid, m-chloroperbenzoic acid, perphthalic acid, etc.). A suitable solvent is selected in accordance with the kinds of the oxidizing agent, and includes, for example, water, acetic acid, alcohols (e.g. methanol, ethanol, etc.), ketones (e.g. acetone, etc.), ethers (e.g. diethyl ether, dioxane, etc.), halogenated hydrocarbons (e.g. dichloromethane, chloroform, etc.), and the like. The reaction temperature may vary depending on the kinds of the oxidizing agent, but is usually in the range of 0° C. to 100° C., and the reaction period of time is usually in the range of 1 to 72 hours.

The pharmacological activities of the compounds of the present invention are illustrated by the results of the following experiments, which were carried out on the representative compounds of the present invention.

The reference compounds used in the experiments are as follows:

A: Metoclopramide hydrochloride monohydrate, and
B: N-[(4-Ethyl-2-morpholinyl)methyl]-2-methoxybenzamide fumarate which is disclosed in the aforementioned Japanese Patent Publication (unexamined) No. 90274/1978.

TEST 1

Gastric emptying enhancing activity

The test was carried out according to the method of Scarpignato et al. [cf. Arch. int. Pharmacodyn., 246, 286–294 (1980)].

Male Wistar rats, weighing 130–150 g, were fasted for 18 hours before experimentation, and 1.5 ml of a test meal (phenol red 0.05% in a 1.5% aqueous methylcellulose solution) was given by gastric tube. Fifteen minutes after administration of the meal the stomach was removed and the amount of phenol red remaining in the stomach was measured.

The test compounds, dissolved or suspended in a 0.5% tragacanth solution, were orally administered 60 minutes before administration of the test meal. The rate of gastric emptying was calculated according to the amount of phenol red remaining in the stomach, and the activity of the test compounds was expressed in terms of increase in the emptying rate from the control. The number of animals used was 5 for the control and each dose of metoclopramide hydrochloride monohydrate and 4 for each dose of the other test compounds. The results are shown in Table 1.

TABLE 1

Gastric emptying enhancing activity

| Test compound | Dose (p.o.) | Increase (%) | Test compound | Dose (p.o.) | Increase (%) |
|---|---|---|---|---|---|
| 1(1)* | 0.2 mg/kg | 39.5 | 81 | 2.0 mg/kg | 52.9 |
| 1 | 2.0 mg/kg | 49.8 | 86 | 2.0 mg/kg | 55.0 |
| 6 | 2.0 mg/kg | 49.2 | 88 | 0.2 mg/kg | 32.8 |
| 7 | 2.0 mg/kg | 74.0 | 88 | 0.5 mg/kg | 42.9 |
| 8 | 2.0 mg/kg | 44.9 | 88 | 2.0 mg/kg | 53.7 |
| 14 | 2.0 mg/kg | 47.5 | 89 | 2.0 mg/kg | 49.9 |
| 16 | 2.0 mg/kg | 47.3 | 90 | 2.0 mg/kg | 55.4 |
| 18(2) | 2.0 mg/kg | 39.3 | 91 | 2.0 mg/kg | 51.2 |
| 25 | 2.0 mg/kg | 39.1 | 92 | 2.0 mg/kg | 41.0 |
| 28 | 2.0 mg/kg | 42.8 | 93 | 0.5 mg/kg | 46.9 |
| 33 | 2.0 mg/kg | 42.3 | 93 | 2.0 mg/kg | 44.2 |
| 37 | 2.0 mg/kg | 42.2 | 94 | 2.0 mg/kg | 52.0 |
| 52 | 2.0 mg/kg | 52.5 | 95 | 0.2 mg/kg | 34.7 |
| 63(1) | 0.5 mg/kg | 33.9 | 95 | 2.0 mg/kg | 61.6 |
| 63(1) | 2.0 mg/kg | 54.4 | 97 | 2.0 mg/kg | 43.8 |
| 64 | 2.0 mg/kg | 59.9 | 101 | 2.0 mg/kg | 46.4 |
| 65 | 2.0 mg/kg | 54.1 | 102 | 2.0 mg/kg | 46.8 |
| 66(1) | 2.0 mg/kg | 41.3 | 104 | 2.0 mg/kg | 43.8 |
| 67 | 2.0 mg/kg | 57.5 | 105 | 2.0 mg/kg | 52.0 |
| 68(1) | 2.0 mg/kg | 62.7 | 111 | 2.0 mg/kg | 48.7 |
| 70 | 2.0 mg/kg | 57.8 | 115 | 2.0 mg/kg | 45.6 |
| 73 | 0.5 mg/kg | 44.2 | 116 | 0.5 mg/kg | 41.4 |
| 73 | 2.0 mg/kg | 46.2 | 116 | 2.0 mg/kg | 52.4 |
| 74 | 2.0 mg/kg | 46.7 | 119 | 2.0 mg/kg | 48.4 |
| 76 | 2.0 mg/kg | 47.1 | 120 | 2.0 mg/kg | 40.6 |
| 77 | 2.0 mg/kg | 43.8 | 130 | 2.0 mg/kg | 51.8 |
| 79 | 2.0 mg/kg | 51.0 | 132 | 2.0 mg/kg | 50.6 |
| 80(1) | 2.0 mg/kg | 65.6 | 244 | 2.0 mg/kg | 51.8 |
| (Reference compound) | | | | | |
| A | 2.0 mg/kg | 20.7 | B | 2.0 mg/kg | 3.8 |
| A | 5.0 mg/kg | 25.7 | B | 5.0 mg/kg | −1.9 |
| A | 10.0 mg/kg | 30.7 | B | 10.0 mg/kg | 2.1 |

(*)It means the compound of Example 1(1) (hereinafter, the same).

As shown in Table 1, the compounds of this invention exhibited potent gastric emptying enhancing activity at a dose of 2.0 mg/kg or less. The effect was stronger than that of metoclopramide hydrochloride monohydrate. On the other hand, Compound B did not show any effect even at a dose of 10.0 mg/kg.

TEST 2

Acute toxicity

Male ddY mice, weighing 18–25 g, were used in groups of 10 animals each. The test compounds, dissolved or suspended in a 0.5% tragacanth solution, were orally administered at a prescribed dose to the animals. The mortality was observed for 7 days after the administration. The results are shown in Table 2.

TEST 3

Effect on the central nervous system (CNS effect)

Male ddY mice, weighing 18–25 g, were used in groups of 3 animals each. According to the method of Irwin [cf. Psychopharmacologia, 13, 222–227 (1968)], comprehensive observation of behavioral and physiologic states were carried out for 2 hours after the oral treatment with 100 mg/kg of the test compound, dissolved or suspended in a 0.5% tragacanth solution. Liability of the test compounds to the central nervous system effect was expressed with the following marks, according to the total sum of potencies for the individually analyzed effects, such as catalepsy, ptosis, hypolocomotin, etc.

TABLE 2

CNS effect and acute toxicity

| Test compound | CNS effect (100 mg/kg, p.o.) | Dose (p.o.) | No. of the dead/ No. of the total |
|---|---|---|---|
| 1(1)* | − | 1000 mg/kg | 0/10 |
| 6 | − | 1000 mg/kg | 2/10 |
| 8 | − | 1000 mg/kg | 0/10 |
| 18(2) | − | 1000 mg/kg | 6/10 |
| 63(1) | − | 1000 mg/kg | 0/10 |
| 66(1) | − | 1000 mg/kg | 0/10 |
| 67 | − | 1000 mg/kg | 5/10 |
| 68(1) | − | 1000 mg/kg | 0/10 |
| 70 | − | 1000 mg/kg | 0/10 |
| 74 | − | 1000 mg/kg | 0/10 |
| 80(1) | − | 1000 mg/kg | 4/10 |
| 81 | − | 1000 mg/kg | 0/10 |
| 88 | − | 1000 mg/kg | 2/10 |
| 89 | + | 1000 mg/kg | 0/10 |
| 90 | − | 1000 mg/kg | 0/10 |
| 91 | − | 1000 mg/kg | 4/10 |
| 93 | − | 1000 mg/kg | 0/10 |
| 94 | − | 1000 mg/kg | 3/10 |
| 95 | − | 1000 mg/kg | 0/10 |
| 97 | − | 1000 mg/kg | 0/10 |
| 101 | − | 1000 mg/kg | 2/10 |
| 104 | − | 1000 mg/kg | 3/10 |
| 105 | − | 1000 mg/kg | 0/10 |
| 116 | − | 1000 mg/kg | 1/10 |
| 119 | − | 1000 mg/kg | 5/10 |
| (Reference compound) | | | |
| A | +++ | 200 mg/kg | 5/10 |

(*)It means the compound of Example 1(1) (hereinafter, the same).
−: No effect
+: Slight effect
++: Moderate effect
+++: Remarked effect As shown in Table 2, both CNS effect and acute toxicity of the compounds of this invention were weaker than those of metoclopramide hydrochloride monohydrate. These data suggest that the present compounds have a good separation between the dose for gastric emptying and that for adverse CNS effects.

As is clear from the above experimental results, the compounds of the formula (I) and pharmaceutically acceptable acid addition salts, quaternary ammonium salts, or N-oxide derivatives thereof have excellent gastrointestinal motility enhancing activity with less toxicity, and hence, are useful as a gastrointestinal motility enhancing agent. They can be used in the prophylaxis and treatment of disorders associated with gastrointestinal motor impairment in mammals including human being, such as dyspepsia, esophageal reflux, gastric stasis, anorexia, nausea, vomiting, and abdominal discomfort which are seen in acute and chronic gastritis, gastric and duodenal ulcers, gastric neurosis, gastroptosis, and the like. They can also be used in the prophylaxis and treatment of esophageal and biliary duct disorders and constipation. Further, they can be used in the prophylaxis and treatment of nausea and vomiting associated with emetogenic cancer chemotherapeutic agents such as cisplatin.

The compounds of the formula (I) and pharmaceutically acceptable acid addition salts, quaternary ammonium salts, or N-oxide derivatives thereof can be administered by oral, parenteral or intrarectal route. The clinical dose of the compounds (I) and pharmaceutically acceptable salts or N-oxide derivatives thereof may vary according to the kinds of the compounds, administration routes, severity of disease, age of patients, or the like, but is usually in the range of 0.001 to 20 mg per kg of body weight per day, preferably 0.004 to 5 mg per kg of body weight per day, in human. The dose may be divided and administered in two or several times per day.

The compounds of the formula (I) and pharmaceutically acceptable salts or N-oxide derivatives thereof are usually administered to patients in the form of a pharmaceutical composition which contains a non-toxic and effective amount of the compounds. The pharmaceutical composition is usually prepared by admixing the active compounds (I), their salts or N-oxide derivatives with conventional pharmaceutical carrier materials which are unreactive with the active compounds (I), their salts or N-oxide derivatives. Suitable examples of the carrier materials are lactose, glucose, mannitol, dextrin, cyclodextrin, starch, sucrose, magnesium aluminosilicate tetrahydrate, synthetic aluminum silicate, microcrystalline cellulose, sodium carboxymethylcellulose, hydroxypropylstarch, calcium carboxymethylcellulose, ion exchange resin, methylcellulose, gelatin, acacia, pullulan, hydroxypropylcellulose, low substituted hydroxypropylcellulose, hydroxypropyl methylcellulose, polyvinylpyrrolidone, polyvinyl alcohol, light anhydrous silicic acid, magnesium stearate, talc, tragacanth, bentonite, veegum, carboxyvinyl polymer, titanium dioxide, sorbitan fatty acid ester, sodium lauryl sulfate, cacao butter, glycerin, glycerides of saturated fatty acids, anhydrous lanolin, glycerogelatin, polysorbate, macrogol, vegetable oils, wax, propylene glycol, water, or the like.

The pharmaceutical composition may be in the dosage form of tablets, capsules, granules, fine granules, powders, syrups, suspension, suppositories, injections, or the like. These preparations may be prepared by conventional methods. Liquid preparations may be prepared by dissolving or suspending the active compounds in water or other suitable vehicles, when used. Tablets, granules and fine granules may be coated in a conventional manner.

The pharmaceutical composition may contain as the active ingredient the compound of the formula (I), its pharmaceutically acceptable salt or N-oxide derivative in the ratio of 0.5% by weight or more, preferably 1 to 70% by weight, based upon the whole weight of the composition. The composition may further contain one or more other therapeutically active compounds.

This invention is illustrated by the following Examples and Reference Examples, but should not be construed to be limited thereto. The identification of the compounds is carried out by elementary analysis, mass spectrum, IR spectrum, NMR spectrum, and the like.

In Examples and Reference Examples, the following abbreviations are somtimes used.

Me: methyl
Et: ethyl
Pr: propyl
Ph: phenyl
Ac: acetyl
A: ethanol
AC: acetone
AE: ethyl acetate
CH: chloroform
DO: dioxane
DM: dichloromethane
E: diethyl ether
H: hexane
IP: isopropyl alcohol
M: methanol
PE: diisopropyl ether
T: toluene.

EXAMPLE 1

Preparation of 4-amino-5-chloro-2-ethoxy-N-[[4-(4-fluorobenzyl)-2-morpholinyl]methyl]benzamide (1) To a solution of 2-aminomethyl-4-(4-fluorobenzyl)morpholine (2.5 g) in dichloromethane (50 ml), 4-amino-5-chloro-2-ethoxybenzoic acid (2.7 g) and 1-ethyl-3-(3-dimethylaminopropyl)carbodiimide hydrochloride (2.4 g) are added, and the mixture is stirred at 25° C. for 4 hours. The reaction mixture is washed successively with water, aqueous sodium hydroxide solution and saturated aqueous sodium chloride solution, dried over magnesium sulfate, and evaporated under reduced pressure. The residue is recrystallized from ethanol to give the title compound (3.0 g), mp 151°–153° C.

(2) The free base (2.0 g) obtained in part (1) of this Example is dissolved in ethanol (50 ml), and 35% ethanolic hydrogen chloride (5 ml) is added. The precipitate is collected and recrystallized from ethanol to give the hydrochloride (1.6 g) of the title compound, mp 160°–163° C.

(3) The free base (7.0 g) obtained in the same manner as in part (1) of this Example is dissolved in hot ethanol (100 ml), and citric acid monohydrate (3.8 g) is added. The mixture is heated to become a clear solution, which is concentrated to 20 ml and cooled. The precipitate is collected and recrystallized from ethanol to give the citrate (8.6 g) of the title compound, mp 143°–145° C.

(4) The free base (1.0 g) obtained in the same manner as in part (1) of this Example is dissolved in hot 10% aqueous citric acid solution (40 ml), and the resulting solution is allowed to cool. The precipitate is collected to give the citrate dihydrate (1.1 g) of the title compound, mp 110°–113° C.

EXAMPLE 2

Preparation of
4-amino-5-chloro-2-ethoxy-N-[[4-(4-fluorobenzyl)-2-morpholinyl]methyl]benzamide (the same compound as that of Example 1)

To a stirred suspension of 4-amino-5-chloro-2-ethoxybenzoic acid (2.9 g) in dichloromethane (50 ml), triethylamine (1.6 g) is added at 25° C. The resulting mixture is cooled to −10° C., and isobutyl chloroformate (2.0 g) is added slowly. After the mixture is stirred at the same temperature for 1 hour, a solution of 2-aminomethyl-4-(4-fluorobenzyl)morpholine (3.0 g) in dichloromethane (10 ml) is added. The reaction mixture is stirred for 1 hour at a temperature of between −10° C. and −5° C. and then at 25° C. overnight. The mixture is washed successively with water, 10% aqueous sodium hydroxide solution and saturated aqueous sodium chloride solution, dried over magnesium sulfate, and evaporated under reduced pressure. The residue is recyrstallized from ethanol to give the title compound (4.1 g), mp 151°–153° C.

EXAMPLE 3

Preparation of
4-amino-N-[3-(4-benzyl-2-morpholinyl)propyl]-5-chloro-2-methoxybenzamide To a mixture of 2-(3-aminopropyl)-4-benzylmorpholine (2.0 g), 4-amino-5-chloro-2-methoxybenzoic acid (1.7 g) and dichloromethane (40 ml), 1-ethyl-3-(3-dimethylaminopropyl)carbodiimide hydrochloride (1.8 g) is added, and the mixture is stirred at 25° C. for 4 hours. The reaction mixture is washed successively with water, 10% aqueous sodium hydroxide solution and saturated aqueous sodium chloride solution, dried over magnesium sulfate, and evaporated under reduced pressure. The residue is dissolved in chloroform and chromatographed on silica gel. The eluate with chloroform is discarded, and the subsequent eluates with methanol-chloroform (1:9) are pooled and evaporated to give the title compound (2.5 g) as an oil.

The free base thus obtained is dissolved in ethanol (50 ml), and a solution of oxalic acid (0.6 g) in ethanol (10 ml) is added. The resulting solution is concentrated to about 10 ml, and diethyl ether is added until a turbidity appears. The precipitate is collected and recrystallized from ethanol to give the oxalate hemihydrate of the title compound, mp 118°–121° C.

EXAMPLE 4

Preparation of
3,4-methylenedioxy-N-[(4-benzyl-2-morpholinyl)methyl]benzamide

A mixture of 3,4-methylenedioxybenzoic acid (2.0 g), thionyl chloride (1.7 g), dimethylformamide (1 drop), and chloroform (25 ml) is refluxed with stirring for 1 hour. After removal of the chloroform under reduced pressure, touene (20 ml) is added and the resulting solution is evaporated under reduced pressure. The residue is dissolved in chloroform (25 ml), and triethylamine (10 ml) is added. To the mixture, a solution of 2-aminomethyl-4-benzylmorpholine (2.5 g) in chloroform (25 ml) is added dropwise at 0° C. The reaction mixture is stirred at 25° C. overnight and then washed successively with water, 1N aqueous sodium hydroxide solution and saturated aqueous sodium chloride solution, and dried over magnesium sulfate. The solvent is distilled off under reduced pressure to give the title compound (4.0 g). The free base thus obtained is treated with fumaric acid in hot isopropyl alcohol. The precipitate is collected and recrystallized from isopropyl alcohol to give the ¾ fumarate of the title compound, mp 161°–163° C.

EXAMPLE 5

Preparation of
4-amino-5-chloro-N-[(4-ethoxycarbonyl-2-morpholinyl)methyl]-2-methoxybenzamide To a solution of 2-aminomethyl-4-ethoxycarbonylmorpholine (5.8 g) in dichloromethane (100 ml), 4-amino-5-chloro-2-methoxybenzoic acid (5.0 g) and 1-ethyl-3-(3-dimethylaminopropyl)carbodiimide hydrochloride (5.2 g) are added, and the resulting mixture is stirred at 25° C. for 4 hours. The reaction mixture is washed successively with water, aqueous sodium hydroxide solution and saturated aqueous sodium chloride solution, and dried over magnesium sulfate. The solvent is distilled off under reduced pressure. The residue is dissolved in chloroform and chromatographed on silica gel. The eluate with chloroform is discarded, and the subsequent eluates with methanol-chloroform (1:9) are pooled and evaporated to give the title compound (7.5 g) as an oil.

The free base thus obtained is treated with oxalic acid in substantially the same manner as in the second paragraph of Example 3 to give the oxalate of the title compound, mp 140°–151° C. (recrystallized from ethanol-diethyl ether).

EXAMPLE 6

Preparation of
4-amino-5-chloro-N-[[4-(4-cyanobenzyl)-2-morpholinyl]methyl]-2-methoxybenzamide (1) To a solution of 2-aminomethyl-4-(4-cyanobenzyl)morpholine (1.5 g) in dichloromethane (40 ml), 4-amino-5-chloro-2-methoxybenzoic acid (1.2 g) and 1-ethyl-3-(3-dimethylaminopropyl)carbodiimide hydrochloride (1.3 g) are added, and the resulting mixture is stirred at 25° C. for 3 hours. The reaction mixture is washed successively with water, aqueous sodium hydroxide solution and saturated aqueous sodium chloride solution, and dried over magnesium sulfate. The solvent is distilled off under reduced pressure to give the title compound as an oil.

(2) The free base obtained in part (1) of this Example is dissolved in a small amount of ethanol, and a solution of fumaric acid (0.7 g) in ethanol (20 ml) is added. The resulting solution is concentrated to about 10 ml and cooled. The precipitate is collected and recrystallized from ethanol to give the fumarate of the title compound, mp 163°–167° C.

EXAMPLE 7

Preparation of
4-acetylamino-5-chloro-2-ethoxy-N-[[4-(4-fluorobenzyl)-2-morpholinyl]methyl]benzamide:

To a stirred mixture of 4-acetylamino-5-chloro-2-ethoxybenzoic acid (2.0 g), 2-aminomethyl-4-(4-fluorobenzyl)morpholine (1.6 g), and dichloromethane (20 ml) is added 1-ethyl-(3-dimethylaminopropyl)carbodiimide hydrochloride (1.5 g), and the resulting mixture is stirred at 25° C. for 1.5 hours. The reaction mixture is washed successively with water, aqueous sodium hydroxide solution and saturated aqueous sodium chloride solution, dried over magnesium sulfate, and evaporated. The residue is recrystallized from ethanol to give the title compound (2.1 g), mp 161°–163° C.

EXAMPLE 8

Preparation of 4-amino-N-[2-(4-benzyl-2-morpholinyl)ethyl]-5-chloro-2-ethoxybenzamide The title compound is prepared in substantially the same manner as in Example 1(1), using 2-(2-aminoethyl)-4-benzylmorpholine in place of 2-aminomethyl-4-(4-fluorobenzyl)morpholine in Example 1(1), mp 149°–151° C. (recrystallized from methanol).

EXAMPLE 9

Preparation of 4-amino-N-[2-(4-benzyl-2-morpholinyl)ethyl]-5-chloro-2-methoxybenzamide The title compound is prepared in substantially the same manner as in Example 6(1), using 2-(2-aminoethyl)-4-benzylmorpholine in place of 2-aminomethyl-4-(4-cyanobenzyl)morpholine in Example 6(1). The free base thus obtained is treated in substantially the same manner as in Example 6(2) to give the hemifumarate 3/2 EtOH, mp 68°–72° C. (recrystallized from ethanol-diethyl ether).

EXAMPLE 10

Preparation of 4-amino-N-[2-[4-(4-cyanobenzyl)-2-morpholinyl)ethyl]-5-chloro-2-methoxybenzamide The ¼ hydrate of the title compound is prepared in substantially the same manner as in Example 6(1), using 2-(2-aminoethyl)-4-(4-cyanobenzyl)morpholine in place of 2-aminomethyl-4-(4-cyanobenzyl)morpholine in Example 6(1), mp 180°–182° C. (recrystallized from isopropyl alcohol).

EXAMPLE 11

Preparation of 2,3-methylenedioxy-N-[(4-benzyl-2-morpholinyl)methyl]benzamide

The title compound is prepared in substantially the same manner as in Example 6(1), using 2-aminomethyl-4-benzylmorpholine and 2,3-methylenedioxybenzoic acid, respectively, in place of 2-aminomethyl-4-(4-cyanobenzyl)morpholine and 4-amino-5-chloro-2-methoxybenzoic acid in Example 6(1). The free base thus obtained is treated in substantially the same manner as in Example 6(2) to give the fumarate ¼ hydrate of the title compound, mp 144°–146° C. (recrystallized from ethanol).

EXAMPLE 12

Preparation of 5-chloro-N-[[4-[3-(4-chlorophenoxy)propyl]-2-morpholinyl]methyl]-4-dimethylamino-2-methoxybenzamide The hemihydrate of the title compound is prepared in substantially the same manner as in Example 6(1), using 2-aminomethyl-4-[3-(4-chlorophenoxy)propyl]morpholine and 5-chloro-4-dimethylamino-2-methoxybenzoic acid, respectively, in place of 2-aminomethyl-4-(4-cyanobenzyl)morpholine and 4-amino-5-chloro-2-methoxybenzoic acid in Example 6(1), mp 128°–130° C. (recrystallized from ethanol).

EXAMPLE 13

Preparation of 5-chloro-N-[[4-(4-cyanobenzyl)-2-morpholinyl]methyl]-4-dimethylamino-2-methoxybenzamide The title compound is prepared in substantially the same manner as in Example 6(1), using 5-chloro-4-dimethylamino-2-methoxybenzoic acid in place of 4-amino-5-chloro-2-methoxybenzoic acid in Example 6(1), mp 161°–163° C. (recrystallized from ethanol).

EXAMPLE 14

Preparation of 4-amino-5-chloro-N-[[4-(2-chlorobenzyl)-6-methyl-2-morpholinyl]methyl]-2-ethoxybenzamide (1) To a solution of 2-aminomethyl-4-(2-chlorobenzyl)-6-methylmorpholine (2.2 g) in dichloromethane (50 ml), 4-amino-5-chloro-2-ethoxybenzoic acid (1.9 g) and 1-ethyl-3-(3-dimethylaminopropyl)carbodiimide hydrochloride (1.7 g) are added. The reaction mixture is stirred at 25° C. for 4 hours, washed successively with water, aqueous sodium hydroxide solution and saturated aqueous sodium chloride solution, and dried over magnesium sulfate. The solvent is distilled off under reduced pressure, and the residue is chromatographed on silica gel with ethyl acetate-hexanechloroform (1:1:1) to give the title compound (2.6 g) as an oil.

(2) The free base (2.6 g) obtained in part (1) of this Example is dissolved in ethanol (50 ml), and a solution of fumaric acid (1.5 g) in ethanol (20 ml) is added. The resulting solution is concentrated to about 10 ml. The precipitate is collected and recrystallized from isopropyl alcohol to give the difumarate of the title compound, mp 150°–154° C.

EXAMPLE 15

Preparation of 4-amino-5-chloro-N-[[4-(2-chlorobenzyl)-5,5-dimethyl-2-morpholinyl]methyl]-2-ethoxybenzamide The title compound is prepared in substantially the same manner as in Example 14(1), using 2-aminomethyl-4-(2-chlorobenzyl)-5,5-dimethylmorpholine in place of 2-aminomethyl-4-(2-chlorobenzyl)-6-methylmorpholine in Example 14(1), mp 181°–184° C. (recrystallized from ethanol).

EXAMPLE 16

Preparation of 4-amino-N-[(4-benzyl-hexahydro-1,4-oxazepin-2-yl)methyl]-5-chloro-2-ethoxybenzamide The title compound is prepared in substantially the same manner as in Example 14(1), using 2-aminomethyl-4-benzylhexahydro-1,4-oxazepine in place of 2-aminomethyl-4-(2-chlorobenzyl)-6-methylmorpholine in Example 14(1). The free base thus obtained is treated in substantially the same manner as in Example 14(2) to give the fumarate of the title compound, mp 180°–183° C. (recrystallized from isopropyl alcohol).

EXAMPLE 17

Preparation of 4-amino-5-chloro-2-ethoxy-N-[[4-(4-fluorobenzyl)-2-morpholinyl]methyl]benzamide (the same compound as that of Example 1)

(1) A mixture of 4-acetylamino-5-chloro-2-ethoxybenzoic acid methyl ester (2.7 g) and 2-aminomethyl-4-

(4-fluorobenzyl)morpholine (5.6 g) is heated with stirring at 150° C. for 2 hours. After cooling, the reaction mixture is chromatographed on silica gel with chloroform to give the title compound, mp 151°–153° C. (recrystallized from ethanol).

(2) The title compound is also prepared in substantially the same manner as in part (1) of this Example, using 4-amino-5-chloro-2-ethoxybenzoic acid methyl ester in place of 4-acetylamino-5-chloro-2-ethoxybenzoic acid methyl ester in part (1) of this Example.

EXAMPLES 18 TO 155

Various compounds listed in the following Tables 3 to 6 are prepared in substantially the same manner as in Examples 1 to 7, 14 and 17, using the corresponding starting materials.

TABLE 3

Structure: 4-amino-5-chloro-2-methoxy-N-[(morpholin-2-yl)methyl]benzamide · Q, with N-substituent R on the morpholine nitrogen.

| Ex. | R | Q | m.p. (°C.) | Recryst. Solvent |
|---|---|---|---|---|
| 18 (1) | CH$_2$Ph | — | 148~150 | AC—T |
| (2) | " | HCl | 217~222 | M |
| 19 | CH$_2$-(2-F-C$_6$H$_4$) | hemifumarate | 138~141 | A |
| 20 | CH$_2$-(3-F-C$_6$H$_4$) | difumarate | 185~187 | " |
| 21 (1) | CH$_2$-(4-F-C$_6$H$_4$) | — | 172~185 | " |
| (2) | " | 5/4HCl.7/4H$_2$O | 144~147 | IP |
| 22 | CH$_2$-(4-Cl-C$_6$H$_4$) | difurmate | 175~181 | A |
| 23 | CH$_2$-(4-Br-C$_6$H$_4$) | fumarate | 103~151 | " |
| 24 | CH$_2$-(3,4-Cl$_2$-C$_6$H$_3$) | 1/5H$_2$O | 89~91 | " |
| 25 | CH$_2$-(C$_6$F$_5$) | EtOH | 99~103 | " |
| 26 | CH$_2$-(4-Me-C$_6$H$_4$) | — | 79~82 | " |

TABLE 3-continued

Structure: 5-chloro-4-amino-2-methoxy-N-[(morpholin-2-yl)methyl]benzamide derivative with N-R substituent · Q

| Ex. | R | Q | m.p. (°C.) | Recryst. Solvent |
|---|---|---|---|---|
| 27 | CH₂-(2,4,6-trimethylphenyl) | sesquifumarate | 192~194 | " |
| 28 | CH₂-(3-CF₃-phenyl) | sesquifumarate.1/2H₂O | 96~99 | |
| 29 | CH₂-(4-CF₃-phenyl) | sesquifumarate | 150~167 | " |
| 30 | CH₂-(3-OMe-phenyl) | fumarate.1/4H₂O | 154~156 | A |
| 31 | CH₂-(4-OMe-phenyl) | 1/5H₂O | 61~64 | " |
| 32 | CH₂-(2-CN-phenyl) | — | 162~165 | IP |
| 33 | CH₂-(3-CN-phenyl) | oxalate.4/5H₂O | 168~172 | A |
| 34 | CH₂-(4-NO₂-phenyl) | — | 97~99 | M |
| 35 | CH₂-(4-NH₂-phenyl) | 2i-PrOH.1/2H₂O | 80~85 | IP |
| 36 | (CH₂)₂Ph | 1/4i-PrOH.1/5H₂O | 175~176 | " |
| 37 | CH(Me)Ph | fumarate.1/2H₂O | 171~175 | A |
| 38 | CH(Me)-(4-F-phenyl) | oxalate.1/4H₂O | 228~231 | " |

TABLE 3-continued

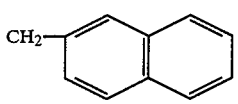

| Ex. | R | Q | m.p. (°C.) | Recryst. Solvent |
|---|---|---|---|---|
| 39 | CHPh₂ | 1/4H₂O | 184~186 | " |
| 40 | CH₂-naphthyl | fumarate.EtOH | 155~158 | A—E |
| 41 | CH₂-furyl | 3/4EtOH | 128~131 | A |
| 42 | CH₃-furyl | hemifumarate.1/4H₂O | 166~168 | A—E |
| 43 | CH₂-thienyl | hemifumarate.1/4EtOH.1/5H₂O | 158~160 | " |
| 44 | CH₂-thienyl | 1/5H₂O | 146~147 | IP—PE |
| 45 | CH₂-(2-pyridyl) | sesquifumarate.H₂O | 88~91 | " |
| 46 | CH₂-(3-pyridyl) | oxalate.5/4EtOH.3/10H₂O | 124~135 | A |
| 47 | CH₂-(4-pyridyl) | — | 167~170 | IP |
| 48 | CH₂-benzisoxazolyl | hemifumarate.1/2H₂O | 127~129 | A |
| 49 | CH₂CH(Me)OPh | oxalate | 113~115 | " |
| 50 | (CH₂)₂O-(4-F-phenyl) | 1/4i-PrOH | 148~150 | IP |
| 51 | (CH₂)₃O-(4-F-phenyl) | 1/2i-PrOH.1/5H₂O | 127~131 | " |

TABLE 3-continued

[Structure: 5-chloro-4-amino-2-methoxy-N-[(morpholin-2-yl)methyl]benzamide with N-R substituent, ·Q salt]

| Ex. | R | Q | m.p. (°C.) | Recryst. Solvent |
|---|---|---|---|---|
| 52 | (CH₂)₃O—C₆H₄—Cl (4-) | — | 123~126 | " |
| 53 | (CH₂)₄O—C₆H₄—F (4-) | sesquifumarate | 158~161 | A—E |
| 54 | (CH₂)₅O—C₆H₄—F (4-) | oxalate.1/4H₂O | 164~166 | A |
| 55 | (CH₂)₆O—C₆H₄—F (4-) | sesquifumarate | 120~122 | A—E |
| 56 | (CH₂)₃O—C₆H₄—CN (4-) | 1/4H₂O | 170~172 | IP |
| 57 | (CH₂)₃O—C₆H₄—NO₂ (4-) | 1/5EtOH | 149~153 | A |
| 58 | (CH₂)₃O—C₆H₄—NH₂ (4-) | oxalate.3/2EtOH.1/2H₂O | 212~216 | " |
| 59 | (CH₂)₃F—C₆H₄—F (4-) | — | 127~130 | IP |
| 60 | CH₂CO—C₆H₄—F (4-) | EtOH.1/5H₂O | 102~106 | A |
| 61 | (CH₂)₃CO—C₆H₄—F (4-) | fumarate | 148~155 | " |
| 62 | CH₂CH=CHPh | sesquifumarate.3/4H₂O | 124~147 | A—E |

TABLE 4

Structure: 4-amino-5-chloro-2-ethoxy-N-[(morpholin-2-yl)methyl]benzamide with R on morpholine N, ·Q

| Ex. | R | Q | m.p. (°C.) | Recryst. Solvent |
|---|---|---|---|---|
| 63 (1) | CH₂Ph | 1/4H₂O | 153~155 | A |
| (2) | " | HCl.3/4H₂O | 200~203 | " |
| 64 | 2-F-C₆H₄-CH₂ | difumarate | 175~178 | IP |
| 65 | 3-F-C₆H₄-CH₂ | fumarate | 183~184 | " |
| 66 (1) | 2-Cl-C₆H₄-CH₂ | — | 144~147 | A |
| (2) | " | HCl.1/2H₂O | 181~183 | " |
| 67 | 3-Cl-C₆H₄-CH₂ | " | 155~158 | " |
| 68 (1) | 4-Cl-C₆H₄-CH₂ | — | 150~151 | " |
| (2) | " | 2HCl | 216~223 | " |
| 69 | C₆F₅-CH₂ | 1/4EtOH | 162~164 | " |
| 70 | 3-CF₃-C₆H₄-CH₂ | — | 146~149 | " |
| 71 | 2-NC-C₆H₄-CH₂ | 3/10H₂O | 154~158 | IP |
| 72 | 3-NC-C₆H₄-CH₂ | oxalate.1/2EtOH.H₂O | 194~198 | A |

TABLE 4-continued

[Structure: 5-chloro-4-amino-2-ethoxy-N-(morpholinylmethyl)benzamide with N-R substituent and Q]

| Ex. | R | Q | m.p. (°C.) | Recryst. Solvent |
|---|---|---|---|---|
| 73 | CH₂-C₆H₄-CN (4-cyanobenzyl) | — | 170~172 | M |
| 74 | CH₂-C₆H₃(Cl)(NO₂) (2-nitro-5-chlorobenzyl) | 1/10CHCl₃.1/5H₂O | 202~205 | CH |
| 75 | (CH₂)₃Ph | oxalate.7/4H₂O | 138~141 | A |
| 76 | (CH₂)₄Ph | oxalate.3/2H₂O | 168~174 | " |
| 77 | CH(Me)Ph | oxalate.3/4H₂O | 135~137 | A—E |
| 78 | CH(Me)-C₆H₄-Cl | — | 131~141 | IP |
| 79 | CH₂-(2-pyridyl) | fumarate | 182~185 | " |
| 80 (1) | CH₂-(3-pyridyl) | fumarate.1/2i-PrOH | 150~152 | " |
| (2) | " | dimaleate.1/2H₂O | 133~135 | A |
| 81 | CH₂-(4-pyridyl) | — | 175~176 | IP |
| 82 | (CH₂)₂O-C₆H₄-Cl | oxalate.1/2 EtOH.1/4H₂O | 186~188 | A |
| 83 | (CH₂)₃O-C₆H₄-Cl | — | 149~151 | " |
| 84 | (CH₂)₃O-C₆H₄-F | 3/4oxalate.2H₂O | 135~138 | M |
| 85 | Ph | 1/4H₂O | 163~165 | IP |

TABLE 5

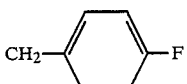

| Ex. | R₁ | R | Q | m.p. (°C.) (Recryst Solvent) |
|---|---|---|---|---|
| 86 | O(CH$_2$)$_2$Me | CH$_2$Ph | fumarate.¼H$_2$O | 192~195 (A) |
| 87 | OCHMe$_2$ | " | fumarate.½H$_2$O | 184~186 (A) |
| 88 | O(CH$_2$)$_3$Me | " | " | 188~190 (A) |
| 89 | " | 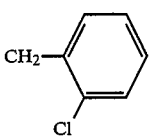 | HCl.7/4H$_2$O | 178~184 (A) |
| 90 | " | 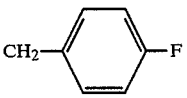 | HCl.½H$_2$O | 196~201 (A) |
| 91 | OCH$_2$CHMe$_2$ | CH$_2$Ph | fumarate | 172~174 (A) |
| 92 | O(CH$_2$)$_4$Me | " | fumarate.½H$_2$O | 172~174 (A) |
| 93 | O(CH$_2$)$_2$CHMe$_2$ | " | " | 175~177 (A) |
| 94 | " | 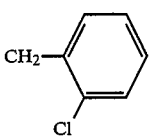 | HCl.2/5EtOH.3/2H$_2$O | 189~195 (A) |
| 95 | " | 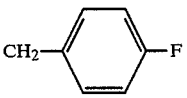 | 2HCl.EtOH | 186~191 (A) |
| 96 | O(CH$_2$)$_5$Me | CH$_2$Ph | sesquifumarate | 188~190 (A) |
| 97 | O(CH$_2$)$_6$Me | " | sesquifumarate.½H$_2$O | 190~193 (A) |
| 98 | O(CH$_2$)$_7$Me | CH$_2$Ph | sesquifumarate.½H$_2$O | 189~192 (A) |
| 99 | O(CH$_2$)$_8$Me | " | 7/4fumarate | 170~172 (A) |
| 100 | O(CH$_2$)$_9$Me | " | " | 166~168 (A) |
| 101 | 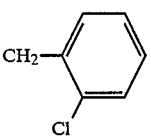 | " | fumarate | 194~197 (A) |
| 102 | O(CH$_2$)$_2$Cl | " | 1/10EtOH.¼H$_2$O | 131~133 (A) |
| 103 | O(CH$_2$)$_3$OH | " | ¼H$_2$O | 154~156 (AE) |
| 104 | OCH$_2$COMe | " | fumarate.H$_2$O | 133~135 (A) |
| 105 | OCH$_2$CH(OH)Me | " | hemifumarate.¾H$_2$O | 94~97 (A) |
| 106 | OCH$_2$O(CH$_2$)$_2$OMe | " | difumarate | 153~156 (IP) |
| 107 | OCH$_2$CN | " | fumarate.¼H$_2$O | 198~201 (A) |
| 108 | OCH$_2$CO$_2$Et | " | — | 138~140 (IP) |
| 109 | 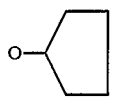 | " | fumarate.½H$_2$O | 139~143 (M) |
| 110 | O(CH$_2$)$_3$NH$_2$ | " | H$_2$O | 77~79 (AE) |
| 111 | 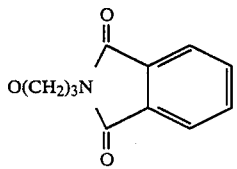 | " | fumarate.¼H$_2$O | 201~204 (A) |

TABLE 5-continued

Structure: 4-chloro-5-amino (H2N at 4-position, Cl at 5-position) benzamide CONHCH2-[morpholine with N-R]·Q, with R1 at the 2-position

| Ex. | R1 | R | Q | m.p. (°C.) (Recryst Solvent) |
|---|---|---|---|---|
| 112 | OCH2-cyclohexyl | CH2Ph | trifumarate | 144~146 (A) |
| 113 | OCH2Ph | " | oxalate.H2O | 103~108 (A-E) |
| 114 | O(CH2)3Ph | " | fumarate.H2O | 85~88 (A) |
| 115 | OCH2CH=CH2 | " | fumarate.¼H2O | 177~180 (IP) |
| 116 | OCH2CH=CMe2 | " | 3/2fumarate.¼H2O | 155~159 (A-IP) |
| 117 | " | CH2-C6H4-4-F | difumarate | 170~172 (A) |
| 118 | " | CH2-C6H4-2-Cl | fumarate.½H2O | 138~141 (A-IP) |
| 119 | O(CH2)2CH=CH2 | CH2Ph | fumarate.¼H2O | 189~192 (A) |
| 120 | OCH2C≡CH | " | difumarate.½H2O | 143~147 (A) |
| 121 | O(CH2)5O-C6H4-4-F | " | fumarate.3/2H2O | 145~147 (A) |
| 122 | OCH2COPh | " | fumarate.½H2O | 207~210 (A) |
| 123 | O(CH2)3CO-C6H4-4-F | " | sesquifumarate.¾H2O | 202~205 (A) |

TABLE 6

Structure: benzamide with R4, R3, R1 substituents, CONHCH2-[morpholine with N-CH2Ph]·Q

| Ex. | R1 | R3 | R4 | Q | m.p.(°C.) (Recryst. Solvent) |
|---|---|---|---|---|---|
| 124 | OH | NH2 | Cl | H2O | 153~155 (IP) |
| 125 | " | NHAc | " | — | 155~157 (IP) |
| 126 | OMe | " | NO2 | ¼H2O | 143~146 (A) |
| 127 | " | NH2 | " | " | 188~194 (M) |
| 128 | " | " | Br | — | 147~149 (AC—T) |
| 129 | " | NHMe | Cl | fumarate·½H2O | 158~162 (A) |
| 130 | " | NMe2 | " | ¾fumarate·¼H2O | 132~134 (IP) |
| 131 | " | NEt2 | " | oxalate.H2O | 73~77 (A—E) |
| 132 | OEt | NMe2 | " | oxalate·½EtOH.¾H2O | 188~191 (A) |
| 133 | OH | " | " | oxalate·½H2O | 123~130 (A—E) |
| 134 | OMe | NHAc | H | H2O | 108~113 (IP) |
| 135 | " | NH2 | " | — | 119~122 (IP—H) |
| 136 | OMe | Cl | NO2 | — | 156~159 (T) |
| 137 | " | H | SO2NH2 | — | 170~173 (IP) |
| 138 | OEt | " | " | — | 221~224 (DO—H2O) |
| 139 | SEt | " | " | — | 195~197 (DO—H2O) |

TABLE 6-continued $$R_4\text{-}\underset{R_3}{\underset{|}{\bigcirc}}\text{-}\underset{R_1}{\underset{|}{\bigcirc}}\text{-}CONHCH_2\text{-}\underset{\underset{CH_2Ph}{|}}{\underset{N}{\bigcirc}}\text{-}O\quad\cdot Q$$

| Ex. | R$_1$ | R$_3$ | R$_4$ | Q | m.p.(°C.) (Recryst. Solvent) |
|---|---|---|---|---|---|
| 140 | Cl | " | " | — | 156~159 (IP) |
| 141 | OMe | Cl | H | HCl | 176~180 (IP—AC) |
| 142 | NH$_2$ | " | " | — | 124~125 (A) |
| 143 | " | NO$_2$ | " | fumarate·½Me$_2$CO | 146~151 (AC) |
| 144 | " | H | NO$_2$ | — | 134 (A) |
| 145 | F | " | SO$_2$NH$_2$ | — | 186~187 (A) |
| 146 | NH$_2$ | Cl | NO$_2$ | fumarate·½Me$_2$CO | 122~127 (AC) |
| 147 | NHMe | H | " | — | 151~154 (A) |
| 148 | NHCH$_2$Ph | " | " | fumarate | 189~195 (IP) |
| 149 | NH(CH$_2$)$_5$Me | " | " | 4/3fumarate | 70~81 (PE) |
| 150 | NH$_2$ | NHMe | NO$_2$ | ¼H$_2$O | 94~105 (DM—H) |
| 151 | " | NMe$_2$ | " | HCl.1/3i-PrOH | 250~265 (IP) |
| 152 | " | H | Br | — | 164~167 (A) |
| 153 | NHMe | " | SO$_2$NH$_2$ | — | 89~94 (A) |
| 154 | NH-◁ | " | " | ¾H$_2$O | 104~107 (M) |
| 155 | NHMe | " | SO$_2$NMe$_2$ | — | 145~146 (A) |

EXAMPLE 156

Preparation of 4-amino-5-chloro-2-methoxy-N-(2-morpholinylmethyl)benzamide (1) A mixture of 4-amino-5-chloro-N-[(4-ethoxycarbonyl-2-morpholinyl)methyl]-2-methoxybenzamide (6.1 g), potassium hydroxide (10.1 g), and isopropyl alcohol (60 ml) is refluxed with stirring for 3 hours. The reaction mixture is concentrated under reduced pressure, and the residue is diluted with water and extracted with chloroform. The organic layer is washed successively with water and saturated aqueous sodium chloride solution, and dried over magnesium sulfate. The solvent is distilled off under reduced pressure, and the residue is recrystallized from isopropyl alcohol to give the title compound (1.4 g), mp 161°-162° C.

(2) A mixture of 4-amino-N-[(4-benzyl-2-morpholinyl)methyl]-5-chloro-2-methoxybenzamide (5.0 g), ethanol (100 ml), and acetic acid (20 ml) is hydrogenated over 10% palladium on carbon (0.5 g) at 25° C. After the calculated amount of hydrogen is absorbed, the catalyst is filtered off. The filtrate is evaporated under reduced pressure to give the title compound (3.8 g).

EXAMPLE 157

Preparation of 4-acetylamino-5-chloro-2-ethoxy-N-[[4-(4-fluorobenzyl)-2-morpholinyl]methyl]benzamide (the same compound as that of Example 7)

To a stirred solution of 4-acetylamino-2-ethoxy-N-[[4-(4-fluorobenzyl)-2-morpholinyl]methyl]benzamide (4.0 g) in dimethylformamide (20 ml) is N-chlorosuccinimide (1.3 g), and the resulting mixture is stirred at 70° C. for 2 hours. The reaction mixture is poured into ice-water and extracted with diethyl ether. The organic layer is washed successively with water and saturated aqueous sodium chloride solution, dried over magnesium sulfate, and evaporated. The residue is recrystallized from acetone to give the title compound (3.1 g), mp 161°-163° C.

The starting material, 4-acetylamino-2-ethoxy-N-[[4-(4-fluorobenzyl)-2-morpholinyl]methyl]benzamide, is prepared in substantially the same manner as in Example (1(1), using 4-acetylamino-2-ethoxybenzoic acid in place of 4-amino-5-chloro-2-ethoxybenzoic acid in Example 1(1).

EXAMPLE 158

Preparation of 4-amino-5-chloro-2-ethoxy-N-[[4-(4-fluorobenzyl)-2-morpholinyl]methyl]benzamide (the same compound as that of Example 1)

(1) A mixture of 4-acetylamino-5-chloro-2-ethoxy-N-[[4-(4-fluorobenzyl)-2-morpholinyl]methyl]benzamide (2.0 g) and 10% hydrochloric acid (40 ml) is refluxed with stirring for 1 hour and cooled. The reaction mixture is neutralized with aqueous sodium hydroxide solution and extracted with chloroform. The organic layer is dried over magnesium sulfate and evaporated. The residue is recrystallized from ethanol to give the title compound (1.4 g), mp 151°-153° C.

(2) The free base (1.0 g) obtained in part (1) of this Example is dissolved in ethanol (25 ml), and 35% ethanolic hydrogen chloride (3 ml) is added. The precipitate is collected and recrystallized from ethanol to give the hydrochloride (0.8 g) of the title compound, mp 160°-163° C.

(3) The free base (1.0 g) obtained in the same manner as in part (1) of this Example is dissolved in hot ethanol (15 ml), and citric acid monohydrate (0.53 g) is added. The mixture is heated to become a clear solution, which is concentrated to 3 ml and cooled. The precipitate is collected and recrystallized from ethanol to give the citrate (1.2 g) of the title compound, mp 143°-145° C.

(4) The free base (1.0 g) obtained in the same manner as part (1) of this Example is dissolved in hot 10% aqueous citric acid solution (40 ml), and the resulting solution is allowed to cool. The precipitate is collected to give the citrate dihydrate (1.1 g) of the title compound, mp 110°–113° C.

EXAMPLES 159 TO 185

The compounds of Examples 18 to 22, 45 to 47, 52, 63 to 68, 79 to 81, 83, and 88 to 95 are prepared by chlorinating the appropriate 4-acetylaminobenzamide derivatives in substantially the same manner as in Example 157 and subsequently hydrolyzing the resulting 4-acetylamino-5-chlorobenzamide derivatives, in substantially the same manner as in Example 158.

EXAMPLE 186

Preparation of 4-amino-5-chloro-2-ethoxy-N-[[4-(4-fluorobenzyl)-2-morpholinyl]methyl]benzamide (the same compound as that of Example 1)

(1) Stannous chloride dihydrate (5.4 g) is added to a stirred mixture of 5-chloro-2-ethoxy-N-[[4-(4-fluorobenzyl)-2-morpholinyl]methyl]-4-nitrobenzamide (2.2 g), ethanol (30 ml), and ethyl acetate (30 ml). The reaction mixture is stirred at 70° C. for 2 hours and concentrated. The residue is basified with aqueous potassium carbonate solution and extracted with ethyl acetate. The organic layer is washed successively with water and saturated aqueous sodium chloride solution, dried over magnesium sulfate, and evaporated. The residue is recrystallized from ethanol to give the title compound (1.1 g), mp 151°–153° C.

The starting material, 5-chloro-2-ethoxy-N-[[4-(4-fluorobenzyl)-2-morpholinyl]methyl]-4-nitrobenzamide, is prepared in substantially the same manner as in Example 1(1), using 5-chloro-2-ethoxy-4-nitrobenzoic acid in place of 4-amino-5-chloro-2-ethoxybenzoic acid in Example 1(1).

(2) The free base (1.0 g) obtained in part (1) of this Example is dissolved in ethanol (25 ml), and 35% ethanolic hydrogen chloride (3 ml) is added. The precipitate is collected and recrystallized from ethanol to give the hydrochloride (0.8 g) of the title compound, mp 160°–163° C.

(3) The free base (1.0 g) obtained in the same manner as in part (1) of this Example is dissovled in hot ethanol (15 ml), and citric acid monohydrate (0.53 g) is added. The mixture is heated to become a clear solution, which is concentrated to 3 ml and cooled. The precipitate is collected and recrystallized from ethanol to give the citrate (1.2 g) of the title compound, mp 143°–145° C.

(4) The free base (1.0 g) obtained in the same manner as in part (1) of this Example is dissovled in hot 10% aqueous citric acid solution (40 ml), and the resulting solution is allowed to cool. The precipitate is collected to give the citrate dihydrate (1.1 g) of the title compound, mp 110°–113° C.

EXAMPLES 187 TO 213

The compounds of Examples 18 to 22, 45 to 47, 52, 63 to 68, 79 to 81, 83, and 88 to 95 are prepared in substantially the same manner as in Example 186, using the corresponding 4-nitro compounds.

EXAMPLE 214

Preparation of 4-amino-N-[(4-benzyl-2-morpholinyl)methyl]-5-chloro-2-hydroxybenzamide (the same compound as that of Example 124)

(1) To a mixture of 2-aminomethyl-4-benzylmorpholine (3.1 g), 2-acetoxy-4-acetylamino-5-chlorobenzoic acid (4.0 g), and dichloromethane (40 ml) is added 1-ethyl-3-(3-dimethylaminopropyl)carbodiimide hydrochloride (2.9 g), and the mixture is stirred at 25° C. for 4 hours. The reaction mixture is washed successively with water and saturated aqueous sodium chloride solution, dried over magnesium sulfate, and evaporated under reduced pressure. The residue is dissolved in ethanol (80 ml), and 10% hydrochloric acid (30 ml) is added. The mixture is refluxed with stirring for 2 hours and concentrated under reduced pressure. The residue is neutralized with aqueous sodium bicarbonate solution and extracted with chloroform. The organic layer is washed successively with water and saturated aqueous sodium chloride solution, dried over magnesium sulfate, and evaporated under reduced pressure. The residue is recrystallized from isopropyl alcohol to give the monohydrate of the title compound (3.0 g), mp 153°–155° C.

(2) To a stirred suspension of 60% sodium hydride (0.52 g) in dimethylformamide (20 ml) is added under ice-cooling a solution of ethanethiol (0.81 g) in dimethylformamide (5 ml). After the mixture is stirred at 25° C. for 0.5 hour, 4-amino-N-[(4-benzyl-2-morpholinyl)methyl]-5-chloro-2-methoxybenzamide (3.4 g) is added, and the mixture is stirred at 100° C. for 1 hour. After cooling, the reaction mixture is evaporated under reduced pressure. The residue is diluted with water, washed with chloroform, and neutralized with 10% hydrochloric acid. The precipitate is collected, washed with water, and recrystallized from isopropyl alcohol to give the monohydrate of the title compound (2.3 g), mp 153°–155° C.

The following compounds are prepared in substantially the same manner as in this Example, using the corresponding starting materials:

4-amino-5-chloro-N-[[4-(2-chlorobenzyl)-2-morpholinyl]methyl]-2-hydroxybenzamide, mp 183°–185° C. (recrystallized from ethanol), 4-amino-5-chloro-N-[[4-(3-chlorobenzyl)-2-morpholinyl]methyl]-2-hydroxybenzamide, 4-amino-5-chloro-N-[[4-(4-chlorobenzyl)-2-morpholinyl]methyl]-2-hydroxybenzamide, 4-amino-5-chloro-N-[[4-(2-fluorobenzyl)-2-morpholinyl]methyl]-2-hydroxybenzamide, 4-amino-5-chloro-N-[[4-(3-fluorobenzyl)-2-morpholinyl]methyl]-2-hydroxybenzamide, 4-amino-5-chloro-N-[[4-(4-fluorobenzyl)-2-morpholinyl]methyl]-2-hydroxybenzamide, oil, 4-amino-5-chloro-2-hydroxy-N-[4-(2-pyridyl)methyl-2-morpholinyl]methyl]benzamide, 4-amino-5-chloro-2-hydroxy-N-[[4-(3-pyridyl)methyl-2-morpholinyl]methyl]benzamide, 4-amino-5-chloro-2-hydroxy-N-[[4-(4-pyridyl)methyl-2-morpholinyl]methyl]benzamide, and 4-amino-5-chloro-N-[4-[3-(4-chlorophenoxy)propyl]-2-morpholinyl]methyl]-2-hydroxybenzamide.

EXAMPLE 215

Preparation of 4-amino-N-[(4-benzyl-2-morpholinyl)methyl]-2-butoxy-5-chlorobenzamide (the same compound as that of Example 88)

To a stirred solution of 4-amino-N-[(4-benzyl-2-morpholinyl)methyl]-5-chloro-2-hydroxybenzamide (4.0 g) in 1N aqueous sodium hydroxide solution (32 ml), tetrabutylammonium bromide (3.4 g) and a solution of butyl bromide (4.3 g) in dichloromethane (32 ml) are added. The reaction mixture is stirred at 25° C. for 15 hours and concentrated under reduced pressure. To the residue is added ethyl acetate. The organic layer is washed successively with water and saturated aqueous sodium chloride solution, dried over magnesium sulfate, and evaporated under reduced pressure. The residue is chromatographed on silica gel with methanol-chloroform (5:95) to give the title compound (5.5 g) as an oil. The free base thus obtained is dissolved in hot ethanol (20 ml), and fumaric acid (1.5 g) is added. The solution is stirred for some time. The precipitate is collected and recrystallized from ethanol to give the fumarate hemihydrate (4.6 g) of the title compound, mp 188°–190° C.

EXAMPLES 216 TO 242

The compounds of Examples 1, 18 to 22, 45 to 47, 52, 63 to 68, 79 to 81, 83, and 89 to 95 are prepared in substantially the same manner as in Example 215, using the corresponding starting materials.

EXAMPLE 243

Preparation of 2-[(4-amino-5-chloro-2-ethoxybenzoyl)aminomethyl]-4-(2-chlorobenzyl)-4-methylmorpholinium iodide To a solution of 4-amino-5-chloro-N-[[4-(2-chlorobenzyl)-2-morpholinyl]methyl]-2-ethoxybenzamide (2.4 g) in methanol (100 ml) is added methyl iodide (4.0 g), and the mixture is stirred at 25° C. for 24 hours. To the reaction mixture is added a proper amount of charcoal, and the mixture is heated for some time and filtered. The filtrate is concentrated to about 10 ml under reduced pressure. The precipitate is collected and recrystallized from methanol to give the hemihydrate (1.6 g) of the title compound, mp 184°–188° C.

EXAMPLE 244

Preparation of 4-amino-5-chloro-N-[[4-(2-chlorobenzyl)-2-morpholinyl]methyl]-2-ethoxybenzamide N-oxide To a stirred solution of 4-amino-5-chloro-N-[[4-(2-chlorobenzyl)-2-morpholinyl]methyl]-2-ethoxybenzamide (4.0 g) in methanol (150 ml) is added 30% aqueous hydrogen peroxide (1.2 g). After the mixture is heated under reflux for 8 hours, an additional 30% aqueous hydrogen peroxide (1.2 g) is added, and the reaction mixture is refluxed with stirring for an additional 24 hours. The solvent is distilled off under reduced pressure, and chloroform and water are added to the residue. The mixture is stirred for about 30 minutes. The precipitate is collected and recrystallized from isopropyl alcohol-diisopropyl ether to give the title compound (0.6 g), mp 154°–157° C.

The starting materials used in the foregoing Examples are prepared as follows.

REFERENCE EXAMPLE 1

Preparation of 2-aminomethyl-4-benzylmorpholine (1) A mixture of 4-benzyl-2-chloromethylmorpholine (86.4 g), phthalimide potassium salt (78.0 g), and dimethylformamide (700 ml) is refluxed with stirring for 5 hours. The reaction mixture is poured into ice-water. The resulting precipitate is collected and recrystallized from isopropyl alcohol to give N-[(4-benzyl-2-morpholinyl)methyl]phthalimide (107 g), mp 136°–139° C. The starting material, 4-benzyl-2-chloromethylmorpholine, is prepared according to the method of F. Loftus [Syn. Commun., 10, 59–73 (1980)].

(2) A mixture of the above phthalimide compound (67.2 g), 85% hydrazine hydrate (20.0 g), and ethanol (180 ml) is refluxed with stirring for 30 minutes. The reaction mixture is filtered, and the filtrate is diluted with water and extracted with chloroform. The organic layer is washed with a small amount of water and then with saturated aqueous sodium chloride solution, and dried over magnesium sulfate. The solvent is distilled off under reduced pressure to give the title compound (33.5 g) as an oil. Treatment of the free base with fumaric acid in hot ethanol gives the difumarate of the title compound, mp 166°–170° C.

REFERENCE EXAMPLE 2

Preparation of 2-aminomethyl-4-phenylmorpholine

The title compound is prepared in substantially the same manner as in Reference Example 1(1) and (2), using 2-chloromethyl-4-phenylmorpholine in place of 4-benzyl-2-chloromethylmorpholine in Reference Example 1(1).

REFERENCE EXAMPLE 3

Preparation of 2-aminomethyl-4-benzylmorpholine (1) A mixture of 4-benzyl-2-chloromethylmorpholine (15.0 g), sodium azide (8.6 g), and dimethylformamide (150 ml) is stirred at 130° C. for 2 hours. The reaction mixture is diluted with water and extracted with diethyl ether. The organic layer is washed successively with water and saturated aqueous sodium chloride solution, and dried over magnesium sulfate. The solvent is distilled off under reduced pressure to give 2-azidomethyl-4-benzylmorpholine (15 g) as an oil.

(2) A solution of 2-azidomethyl-4-benzylmorpholine (15 g) in toluene (40 ml) is added dropwise to a stirred solution of 70% sodium bis(2-methoxyethoxy)aluminum hydride in toluene (60 ml) cooled to −5° C. The reaction mixture is stirred at 25° C. for 1.5 hours and cooled to 10° C., and the excess of the reducing agent is decomposed by the cautious addition of 10% aqueous sodium hydroxide solution. The organic layer is separated, washed successively with water and saturated aqueous sodium chloride solution, and dried over magnesium sulfate. After removal of the solvent under reduced pressure, the title compound is obtained a an oil (11 g).

REFERENCE EXAMPLE 4

Preparation of 2-acetylaminomethyl-4-benzylmorpholine

A mixture of N-[(4-benzyl-2-morpholinyl)methyl]phthalimide (162 g), 85% hydrazine hydrate (43.3 g), and ethanol (100 ml) is refluxed with stirring for 20 minutes. The reaction mixture is filtered, and the filtrate is diluted with water and extracted with chloroform. The organic layer is separated, washed with a small amount of water and then with saturated aqueous sodium chloride solution, dried over magnesium sulfate, and filtered. To the filtrate is added slowly acetic anhydride (98.3 g), and the resulting mixture is stirred at 25° C. for 2 hours. The reaction mixture is washed successively with aqueous sodium hydroxide solution, water and saturated aqueous sodium chloride solution, and dried over magnesium sulfate. The solvent is distilled off under reduced pressure, and the residue is recrystallized from toluene to give the title compound (101 g), mp 110°–111° C.

REFERENCE EXAMPLE 5

Preparation of 2-acetylaminomethylmorpholine

2-Acetylaminomethyl-4-benzylmorpholine (120 g) is dissolved in a mixture of ethanol (1000 ml) and acetic acid (30 ml) and hydrogenated over 10% palladium on carbon (5 g) at about 60° C. After the calculated amount of the hydrogen is absorbed, the catalyst is filtered off. The filtrate is evaporated under reduced pressure to give the title compound as an oil.

REFERENCE EXAMPLE 6

Preparation of 2-acetylaminomethyl-4-(4-fluorobenzyl)morpholine

A mixture of 2-acetylaminomethylmorpholine (7.0 g), 4-fluorobenzyl chloride (12 g), potassium carbonate (56 g), potassium iodide (1 g), and methyl ethyl ketone (100 ml) is refluxed with stirring for 17 hours. The reaction mixture is filtered and the filtrate is concentrated under reduced pressure. The residue is diluted with water and extracted with chloroform. The organic layer is separated, washed successively with water and saturated aqueous sodium chloride solution, and dried over magnesium sulfate. The solvent is distilled off under reduced pressure, and the residue is recrystallized from toluene to give the title compound (9.3 g), mp 120°–122° C.

REFERENCE EXAMPLES 7 TO 55

Various compounds listed in Table 7 are prepared in substantially the same manner as in Reference Example 6, using the appropriate alkylating agents in place of 4-fluorobenzyl chloride in Reference Example 6.

TABLE 7

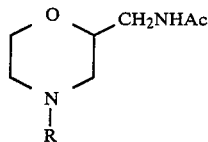

| Ref. Ex. | R | m.p. (°C.) | Recryst. Solvent |
|---|---|---|---|
| 7 | CH₂–(2-F-phenyl) | 111~112 | T |
| 8 | CH₂–(3-F-phenyl) | 108~109 | " |
| 9 | CH₂–(2-Cl-phenyl) | 107~109 | " |
| 10 | CH₂–(3-Cl-phenyl) | 79~82 | " |
| 11 | CH₂–(4-Cl-phenyl) | 93~96 | T–E |
| 12 | CH₂–(4-Br-phenyl) | 92~94 | T–H |
| 13 | CH₂–(2,3-diCl-phenyl) | 89~90 | PE–E |
| 14 | CH₂–(pentafluorophenyl) | 93~96 | T |
| 15 | CH₂–(4-Me-phenyl) | 97~98 | T–H |
| 16 | CH₂–(3,4,5-triMe-phenyl) | 107~108 | T |
| 17 | CH₂–(2-CF₃-phenyl) | 94~95 | " |
| 18 | CH₂–(4-CF₃-phenyl) | oil | |
| 19 | CH₂–(2-OMe-phenyl) | 68~70 | T |

TABLE 7-continued

Structure: morpholine with CH₂NHAc at 2-position and R on N

| Ref. Ex. | R | m.p. (°C.) | Recryst. Solvent |
|---|---|---|---|
| 20 | CH₂-C₆H₄-OMe (4-) | oil | |
| 21 | CH₂-C₆H₄-CN (4-) | 112~113 | T |
| 22 | CH₂-C₆H₄-CN (2-) | 119~122 | " |
| 23 | CH₂-C₆H₄-CN (3-) | 64~67 | E |
| 24 | CH₂-C₆H₄-NO₂ (4-) | oil | |
| 25 | CH₂-C₆H₃(NO₂)(Cl) | " | |
| 26 | (CH₂)₂Ph | " | |
| 27 | (CH₂)₃Ph | " | |
| 28 | (CH₂)₄Ph | " | |
| 29 | CH(Me)Ph | " | |
| 30 | CH(Me)-C₆H₄-F (4-) | " | |
| 31 | CH(Me)-C₆H₄-Cl (4-) | " | |
| 32 | CHPh₂ | 155~157 | T |
| 33 | CH₂-naphthyl | 92~94 | " |
| 34 | CH₂-furan-2-yl | 65~68 | " |
| 35 | CH₂-furan-2-yl | 101~103 | " |
| 36 | CH₂-thiophen-2-yl | 88~92 | " |
| 37 | CH₂-thiophen-3-yl | 112~113 | T |
| 38 | CH₂-pyridin-2-yl | 88~89 | T—E |
| 39 | CH₂-pyridin-3-yl | 105~107 | T |
| 40 | CH₂-pyridin-4-yl | 97~101 | " |
| 41 | CH₂-benzisoxazolyl | oil | |
| 42 | CH₂CH(Me)OPh | " | |
| 43 | (CH₂)₂O-C₆H₄-F (4-) | " | |
| 44 | (CH₂)₃O-C₆H₄-F (4-) | " | |
| 45 | (CH₂)₂O-C₆H₄-Cl (4-) | 97~98 | T |
| 46 | (CH₂)₃O-C₆H₄-Cl (4-) | oil | |
| 47 | (CH₂)₄O-C₆H₄-F (4-) | " | |

TABLE 7-continued

[Structure: morpholine ring with O at top, CH2NHAc substituent at 2-position, N-R at bottom]

| Ref. Ex. | R | m.p. (°C.) | Recryst. Solvent |
|---|---|---|---|
| 48 | (CH₂)₅O—C₆H₄—F | 98~100 | AC |
| 49 | (CH₂)₆O—C₆H₄—F | oil | |
| 50 | (CH₂)₃O—C₆H₄—CN | " | |
| 51 | (CH₂)₃O—C₆H₄—NO₂ | " | |
| 52 | (CH₂)₃S—C₆H₄—F | " | |
| 53 | CH₂CO—C₆H₄—F | " | |
| 54 | (CH₂)₃CO—C₆H₄—F | " | |
| 55 | CH₂CH=CHPh | " | |

REFERENCE EXAMPLE 56

Preparation of 2-aminomethyl-4-(4-fluorobenzyl)morpholine

A solution of 2-acetylaminomethyl-4-(4-fluorobenzyl)morpholine (3.0 g) in 10% hydrochloric acid (50 ml) is refluxed with stirring for 4 hours. The reaction mixture is adjusted to pH 11 with aqueous sodium hydroxide solution and extracted with chloroform. The organic layer is washed successively with water and saturated aqueous sodium chloride solution, and dried over magnesium sulfate. Removal of the solvent under reduced pressure gives the title compound as an oil.

REFERENCE EXAMPLE 57

Preparation of 2-aminomethyl-4-substituted-morpholines

The title compounds are prepared in substantially the same manner as in Reference Example 56, using the products of Reference Examples 4, 7 to 18, 21 to 33, 38 to 41, and 53 to 55 in place of 2-acetylaminomethyl-4-(4-fluorobenzyl)morphoine in Reference Example 56.

REFERENCE EXAMPLE 58

Preparation of 2-aminomethyl-4-[3-(4-chlorophenoxy)propyl]morpholine

A mixture of 2-acetylaminomethyl-4-[3-(4-chlorophenoxy)propyl]morpholine (3.3 g) and 10% aqueous sodium hydroxide solution (60 ml) is refluxed with stirring for 20 hours. The reaction mixture is extracted with chloroform, and the organic layer is washed successively with water and saturated aqueous sodium chloride solution, and dried over magnesium sulfate. Removal of the solvent under reduced pressure gives the title compound as an oil.

REFERENCE EXAMPLE 59

Preparation of 2-aminomethyl-4-substituted-morpholines

The title compounds are prepared in substantially the same manner as in Reference Example 58, using the products of Reference Examples 19, 20, 34 to 37, 42 to 45, 47 to 52, and 55 in place of 2-acetylaminomethyl-4-[3-(4-chlorophenoxy)propyl]morpholine in Reference Example 58.

REFERENCE EXAMPLE 60

Preparation of 2-aminomethyl-4-ethoxycarbonylmorpholine (1) To a stirred solution of N-[(4-benzyl-2-morpholinyl)methyl]phthalimide (30.0 g) in toluene (200 ml), ethyl chloroformate (19.4 g) is added dropwise at 60° C., and the mixture is refluxed with stirring for 1 hour. The reaction mixture is washed successively with water and saturated aqueous sodium chloride solution, and dried over magnesium sulfate. The solvent is distilled off under reduced pressure, and the residue is recrystallized from isopropyl alcohol-diethyl ether to give N-[(4-ethoxycarbonyl-2-morpholinyl)methyl]phthalimide (27.8 g), mp 113°–115° C.

(2) A mixture of N-[(4-ethoxycarbonyl-2-morpholinyl)methyl]phthalimide (10.0 g), 85% hydrazine hydrate (2.9 g), and ethanol (10 ml) is refluxed with stirring for 10 minutes. The reaction mixture is filtered and the filtrate is extracted with chloroform. The organic layer is washed successively with water and saturated aqueous sodium chloride solution, and dried over magnesium sulfate. Removal of the solvent under reduced pressure gives the title compound (5.8 g) as an oil.

REFERENCE EXAMPLE 61

Preparation of 4-benzyl-2-cyanomethylmorpholine

A mixture of 4-benzyl-2-chloromethylmorpholine (22.5 g), potassium cyanide (13 g), potassium iodide (1 g), and dimethyl sulfoxide (40 ml) is heated with stirring at 120° C. for 5 hours. The reaction mixture is cooled, diluted with water, and extracted with diethyl ether. The organic layer is washed with water, dried over sodium sulfate, and evaporated to give the title compound (20 g) as an oil.

REFERENCE EXAMPLE 62

Preparation of 2-(2-aminoethyl)-4-benzylmorpholine

A solution of 4-benzyl-2-cyanomethylmorpholine (20g) in a mixture of ethanol (160 ml) and 28% ammonia water (10 ml) is hydrogenated over Raney nickel (2 g, wet) at 25° C. for 2 hours. The catalyst is filtered off and the filtrate is evaporated under reduced pressure. The residual oil (16.5 g) is treated with a solution of maleic acid in ethanol to give the maleate, which is recrystallized from ethanol-ethyl acetate to give the sesquimaleate of the title compound, mp 123°–125° C.

REFERENCE EXAMPLE 63

Preparation of 2-(2-hydroxyethyl)-4-benzylmorpholine

A solution of 2-ethoxycarbonylmethyl-4-benzylmorpholine (41 g) in diethyl ether (100 ml) is added dropwise to a stirred suspension of lithium aluminum hydride (59.2 g) in diethyl ether (150 ml). The reaction mixture is stirred at 25° C. for 1 hour. The excess of lithium aluminum hydride is decomposed by the successive addition of ethyl acetate and water. The insoluble materials are filtered off, and the filtrate is evaporated to give the title compound (34.4 g) as an oil. The starting material, 2-ethoxycarbonylmethyl-4-benzylmorpholine, is prepared according to the method of F. Loftus [Syn. Commun., 10, 59–73 (1980)].

REFERENCE EXAMPLE 64

Preparation of 2-(2-acetoxyethyl)-4-benzylmorpholine

To a mixture of 2-(2-hydroxyethyl)-4-benzylmorpholine (27.7 g), triethylamine (28 ml), and ethyl acetate (100 ml) is dropwise added acetic anhydride (17.8 ml). The reaction mixture is stirred at 25° C. for 1 hour and evaporated under reduced pressure. The residue is dissolved in chloroform and chromatographed on silica gel. Fractions containing the title compound are pooled and evaporated to give the title compound (29.1 g) as an oil.

REFERENCE EXAMPLE 65

Preparation of 2-(2-acetoxyethyl)-4-benzyloxycarbonylmorpholine

To a solution of 2-(2-acetoxyethyl)-4-benzylmorpholine (29.1 g) in acetonitrile (200 ml) is dropwise added benzyl chloroformate (24.4 g). The reaction mixture is refluxed for 30 minutes, cooled and evaporated under reduced pressure. The residue is chromatographed on silica gel. The eluate with hexane is discarded, and the subsequent eluates with hexane-chloroform (1:1) are pooled and evaporated to give the title compound (24.5 g) as an oil.

REFERENCE EXAMPLE 66

Preparation of 2-(2-hydroxyethyl)-4-benzyloxycarbonylmorpholine

A mixture of 2-(2-acetoxyethyl)-4-benzyloxycarbonylmorpholine (24.5 g), potassium hydroxide (8.9 g), ethanol (40 ml), and water (40 ml) is refluxed for 30 minutes and concentrated under reduced pressure. Water is added to the residue and the mixture is extracted with diethyl ether. The organic layer is washed with water, dried over sodium sulfate, and evaporated to give the title compound (15 g) as an oil.

REFERENCE EXAMPLE 67

Preparation of 2-(2-chloroethyl)-4-benzyloxycarbonylmorpholine

To a mixture of 2-(2-hydroxyethyl)-4-benzyloxycarbonylmorpholine (15 g), dimethylformamide (1 ml), and chloroform (50 ml) is dropwise added thionyl chloride (16.3 ml). The mixture is refluxed for 2 hours, allowed to cool, and evaporated under reduced pressure to give the title compound (16 g) as an oil.

REFERENCE EXAMPLE 68

Preparation of 2-(2-cyanoethyl)-4-benzyloxycarbonylmorpholine

A mixture of 2-(2-chloroethyl)-4-benzyloxycarbonylmorpholine (16 g), potassium cyanide (6.3 g), potassium iodide (1 g), and dimethylformamide (50 ml) is heated at 100° C. with stirring for 5 hours. After cooling, the reaction mixture is diluted with water and extracted with diethyl ether. The organic layer is dried over sodium sulfate and evaporated. The residue is crystallized from diethyl ether-hexane to give the title compound (10.7 g), mp 59°–60° C.

REFERENCE EXAMPLE 69

Preparation of 2-(2-cyanoethyl)morpholine

A solution of 2-(2-cyanoethyl)-4-benzyloxycarbonylmorpholine (10.7 g) in ethanol (60 ml) is hydrogenated over 5% palladium on carbon (1 g) at 25° C. After the calculated amount of hydrogen is absorbed, the catalyst is filtered off. The filtrate is evaporated under reduced pressure to give the title compound (5.4 g) as an oil.

REFERENCE EXAMPLE 70

Preparation of 2-(2-cyanoethyl)-4-benzylmorpholine

A mixture of 2-(2-cyanoethyl)morpholine (5.4 g), benzyl chloride (5.4 g), potassium carbonate (5.4 g), potassium iodide (0.5 g), and methyl ethyl ketone (30 ml) is heated under reflux for 1 hour. After cooling, the reaction mixture is filtered and the filtrate is concentrated. The residue is dissolved in diethyl ether, and the solution is extracted with dilute hydrochloric acid. The extracts are basified with dilute aqueous sodium hydroxide solution and extracted with chloroform. The organic layer is dried over sodium sulfate and evaporated to give the title compound (8 g) as an oil.

REFERENCE EXAMPLE 71

Preparation of 2-(3-aminopropyl)-4-benzylmorpholine

A solution of 2-(2-cyanoethyl)-4-benzylmorpholine (8 g) in a mixture of ethanol (60 ml) and 28% ammonia water (4 ml) is hydrogenated over Raney nickel at 25° C. After the calculated amount of hydrogen is absorbed, the catalyst is filtered off. The filtrate is evaporated under reduced pressure to give the title compound (7 g) as an oil.

REFERENCE EXAMPLE 72

Preparation of 2-(2-chlorobenzyl)amino-1-methylethanol

A mixture of 2-amino-1-methylethanol (25.0 g), 2-chlorobenzaldehyde (51.5 g), sodium bicarbonate (33.6 g), and methanol (1000 ml) is refluxed with stirring for 4 hours. After the reaction mixture is cooled to 10° C., sodium borohydride (13.9 g) is added in small portions, and the resulting mixture is stirred at 25° C. for 1 hour. The solvent is removed under reduced pressure, and the residue is diluted with water and extracted with chloroform. The organic layer is washed successively with water and saturated aqueous sodium chloride solution, and dried over magnesium sulfate. The solvent is distilled off under reduced pressure to give the title compound (55.0 g) as an oil.

REFERENCE EXAMPLE 73

Preparation of 4-(2-chlorobenzyl)-2-chloromethyl-6-methylmorpholine

A mixture of 2-(2-chlorobenzyl)amino-1-methylethanol (20.0 g) and epichlorohydrin (9.7 g) is stirred at 25° C. for 24 hours. To the reaction mixture is added 98% sulfuric acid (30 ml), and the resulting mixture is stirred at 150° C. for 30 minutes. After cooling, the reaction mixture is poured into ice-water. The mixture is basified with aqueous sodium hydroxide solution and extracted with toluene. The organic layer is washed successively with water and saturated aqueous sodium chloride solution, and dried over magnesium sulfate. The solvent is distilled off under reduced pressure to give the title compound (19.7 g) as an oil.

REFERENCE EXAMPLE 74

Preparation of N-[[4-(2-chlorobenzyl)-6-methyl-2-morpholinyl]methyl]phthalimide

A mixture of 4-(2-chlorobenzyl)-2-chloromethyl-6-methylmorpholine (19.7 g), phthalimide potassium salt (14.6 g), and dimethylformamide (150 ml) is stirred at 150° C. for 5 hours. The reaction mixture is poured into ice-water and extracted with diethyl ether. The organic layer is washed successively with water and saturated aqueous sodium chloride solution, and dried over magnesium sulfate. The solvent is distilled off to give the title compound (26 g) as an oil.

REFERENCE EXAMPLE 75

Preparation of 2-acetylaminomethyl-4-(2-chlorobenzyl)-6-methylmorpholine

A mixture of N-[[4-(2-chlorobenzyl)-6-methyl-2-morpholinyl]methyl]phthalimide (26 g), 100% hydrazine hydrate (4.2 g), and ethanol (20 ml) is refluxed with stirring for 15 minutes. After the insoluble materials are filtered off, the filtrate is diluted with water and extracted with chloroform. The organic layer is washed successively with water and saturated aqueous sodium chloride solution, dried over magnesium sulfate, and filtered. Acetic anhydride (14.7 g) is added to the filtrate, and the mixture is stirred at 25° C. for 2 hours. The reaction mixture is washed successively with aqueous sodium hydroxide solution, water and saturated aqueous sodium chloride solution, and dried over magnesium sulfate. After removal of the solvent under reduced pressure, the residue is chromatographed on silica gel with ethyl acetate to give the title compound (15 g) as an oil.

REFERENCE EXAMPLE 76

Preparation of 2-aminomethyl-4-(2-chlorobenzyl)-6-methylmorpholine

A solution of 2-acetylaminomethyl-4-(2-chlorobenzyl)-6-methylmorpholine (3.0 g) in 10% hydrochloric acid (60 ml) is refluxed with stirring for 2 hours. The reaction mixture is basified with aqueous sodium hydroxide solution and extracted with chloroform. The organic layer is washed successively with water and saturated aqueous sodium choride solution, and dried over magnesium sulfate. The solvent is distilled off under reduced pressure to give the title compound (2.2 g) as an oil.

REFERENCE EXAMPLE 77

Preparation of 2-aminomethyl-4-(2-chlorobenzyl)-5,5-dimethylmorpholine 2-(2-Chlorobenzyl)amino-2-methylpropanol is prepared in substantially the same manner as in Reference Example 72, using 2-amino-2-methylpropanol in place of 2-amino-1-methylethanol in Reference Example 72. This product is converted to the oily title compound in substantially the same manner as in Reference Examples 73 to 76.

REFERENCE EXAMPLE 78

Preparation of 2-aminomethyl-4-benzyl-hexahydro-1,4-oxazepine

3-Benzylaminopropanol is prepared in substantially the same manner as in Reference Example 72, using 3-aminopropanol and benzaldehyde, respectively, in place of 2-amino-1-methylethanol and 2-chlorobenzaldehyde in Reference Example 72. This product is converted to the oily title compound in substantially the same manner as in Reference Examples 73 to 76.

REFERENCE EXAMPLE 79

Preparation of 2-acetylaminomethyl-4-(4-fluorobenzyl)morpholine (the same compound of that of Reference Example 6)

A mixture of N-(4-fluorobenzyl)ethanolamine (10.0 g), N-(2,3-epoxypropyl)phthalimide (12.3 g) is stirred at 80° C. for 3 hours. To the reaction mixture is added gradually 98% sulfuric acid (31.9 g), and the mixture is stirred at 150° C. for 2 hours. The resulting brown solution is cooled to 25° C. and poured into ice-water. The mixture is basified with aqueous sodium hydroxide solution and extracted with chloroform. The organic layer is washed successively with water and saturated aqueous sodium chloride solution, dried over magnesium sulfate, and filtered. Acetic anhydride (6.0 g) is added to the filtrate. After the resulting mixture is stirred at 25° C. for 2 hours, ice-water and then aqueous sodium hydroxide solution are added. The mixture is stirred at 25° C. for some time. The organic layer is separated, washed successively with water and saturated aqueous sodium chloride solution, and dried over magnesium sulfate. The solvent is evaporated off and the residue is recrystallized from toluene to give the title compound (8.8 g), mp 120°–122° C.

REFERENCE EXAMPLE 80

Preparation of 4-amino-5-chloro-2-hexyloxybenzoic acid (1) A mixture of p-acetylaminosalicylic acid methyl ester (5.0 g), hexyl iodide (7.6 g), potassium carbonate (9.9 g), and dimethylformamide (20 ml) is stirred at 70° C. for 30 hours. The reaction mixture is poured into ice-water and extracted with diethyl ether. The organic layer is washed successively with aqueous sodium hydroxide solution and saturated aqueous sodium chloride solution, dried over magnesium sulfate, and evaporated. The residue is chromatographed on silica gel with chloroform-methanol (20:1) to give 4-acetylamino-2-hexyloxybenzoic acid methyl ester (4.9 g) as an oil.

(2) To a stirred solution of 4-acetylamino-2-hexyloxybenzoic acid methyl ester (2.6 g) in dimethylformamide (20 ml) is added N-chlorosuccinimide (1.4 g), and the resulting mixture is stirred at 70° C. for 1 hour. The reaction mixture is poured into ice-water and extracted with diethyl ether. The organic layer is washed successively with water and saturated sodium chloride solution, dried over magnesium sulfate, and evaporated to give 4-acetylamino-5-chloro-2-hexyloxybenzoic acid methyl ester (2.1 g) as an oil.

(3) A mixture of 4-acetylamino-5-chloro-2-hexyloxybenzoic acid methyl ester (2.1 g), ethanol (10 ml), and water (30 ml) containing sodium hydroxide (2.6 g) is heated under reflux for 4 hours. The ethanol is distilled off under reduced pressure, and the resulting solution is acidified with dilute hydrochloric acid and extracted with chloroform. The organic layer is treated in the same manner as in part (2) of this Reference Example to give the title compound.

Various compounds used as starting materials in Examples 86 to 95, and 97 to 123 are prepared in substantially the same manner as in this Reference Example, using the appropriate agents in place of hexyl iodide.

REFERENCE EXAMPLE 81

Preparation of 2-benzylamino-5-nitrobenzoic acid

A solution of 2-chloro-5-nitrobenzoic acid (5.0 g) and benzylamine (15.0 g) in ethanol (40 ml) is refluxed for 10 hours and then concentrated under reduced pressure. To the residue is added water (100 ml), and the resulting solution is adjusted to the pH of about 4 with acetic acid and stirred for 1 hour. The precipitate is collected and recrystallized from ethanol to give the title compound (4.8 g), mp 238°–248° C.

REFERENCE EXAMPLE 82

Preparation of 2-hexylamino-5-nitrobenzoic acid

The title compound is prepared in substantially the same manner as in Reference Example 81, using hexylamine in place of benzylamine in Reference Example 81, mp 161°–163° C. (recrystallized from diisopropyl ether-hexane).

REFERENCE EXAMPLE 83

Preparation of -acetylamino-4-dimethylamino-5-nitrobenzoic acid

Accoriding to the method of G. E. Keyser and N. J. Leonard [J. Org. Chem., 44, 2989–2994 (1979)], 2-acetylamino-4-chlorobenzoic acid (33.0 g) is nitrated to give 2-acetylamino-4-chloro-5-nitrobenzoic acid (30.0 g). A solution of the nitrated acid (11.3 g) and 40% aqueous dimethylamine solution (40 ml) in ethanol (100 ml) is refluxed for 5 hours and then evaporated under reduced pressure. To the residue is added water (100 ml), and the resulting solution is adjusted to the pH of about 4 with acetic acid. The precipitate is collected and recrystallized from ethanol to give the title compound (8.6 g), mp 230°–255° C.

REFERENCE EXAMPLE 84

Preparation of 2-amino-4-dimethylamino-5-nitrobenzoic acid

A mixture of 2-acetylamino-4-dimethylamino-5-nitrobenzoic acid (6.5 g), concentrated hydrochloric acid (20 ml), and water (80 ml) is stirred at 100° C. for 30 minutes. After cooling, solid sodium hydroxide (5 g) and then 10% aqueous sodium hydroxide solution are added until the mixture becomes a clear solution. The resulting solution is adjusted to the pH of about 4 with acetic acid. The precipitate is collected and recrystallized from methanol to give the title compound (4.8 g), mp 240°–250° C.

REFERENCE EXAMPLE 85

Preparation of 2-amino-4-methylamino-5-nitrobenzoic acid

A mixture of 2-acetylamino-4-chloro-5-nitrobenzoic acid (10.0 g) and 40% aqueous methylamine solution (60 ml) is stirred at 80° C. for 10 hours and then evaporated under reduced pressure. To the residue is added 40% aqueous methylamine solution (100 ml), and the resulting solution is stirred at 80° C. for 20 hours. After cooling, the mixture is diluted with water (50 ml) and then adjusted to the pH of about 4 with acetic acid. The precipitate is collected and recrystallized from acetonitrile to give the title compound (7.6 g), mp 260°–272° C.

REFERENCE EXAMPLE 86

Preparation of 2-fluoro-5-sulfamoylbenzoic acid

A solution of 5-chlorosulfonyl-2-fluorobenzoic acid (7.0 g) and 28% ammonia water (20 ml) in tetrahydrofuran (70 ml) is stirred at 0° C. for 1.5 hours. The reaction mixture is poured into water (200 ml), acidified with concentrated hydrochloric acid, and extracted with chloroform. The extracts are washed with water, dried over sodium sulfate, and evaporated under reduced pressure. The residue is washed with diethyl ether to give the title compound (5.0 g).

REFERENCE EXAMPLE 87

Preparation of 2-methylamino-5-dimethylsulfamoylbenzoic acid

A mixture of 5-dimethylsulfamoyl-2-fluorobenzoic acid (10 g) and 40% aqueous methylamine solution (85 ml) is refluxed for 24 hours and then evaporated under reduced pressure. The residue is adjusted to the pH of about 4 with acetic acid. The precipitate is collected, washed with water, and dried to give the title compound (6.0 g).

REFERENCE EXAMPLE 88

Preparation of 2-cyclopropylamino-5-sulfamoylbenzoic acid

The title compound is prepared from 2-fluoro-5-sulfamoylbenzoic acid and cyclopropylamine in substantially the same manner as in Reference Example 87.

EXAMPLE 245

| | per 1,000 tablets |
|---|---|
| 4-Amino-5-chloro-2-ethoxy-N—[[4-(4-fluorobenzyl)-2-morpholinyl]methyl]benzamide citrate | 2 g |
| Corn starch | 28 g |
| Lactose | 55 g |
| Microcrystalline cellulose | 11 g |
| Hydroxypropylcellulose | 3 g |
| Light anhydrous silicic acid | 0.5 g |
| Magnesium stearate | 0.5 g |

The above components are blended, granulated and made into 1,000 tablets each weighing 100 mg by a conventional method.

EXAMPLE 246

| | per 1,000 capsules |
|---|---|
| 4-Amino-5-chloro-2-ethoxy-N—[[4-(3-pyridyl)-methyl-2-morpholinyl]methyl]benzamide fumarate | 5 g |
| Corn starch | 103 g |
| Lactose | 65 g |
| Hydroxypropylcellulose | 5 g |
| Light anhydrous silicic acid | 1 g |
| Magnesium stearate | 1 g |

The above components are blended, granulated and filled into 1,000 capsules by a conventional method.

EXAMPLE 247

| | fine granules |
|---|---|
| 4-Amino-N—[(4-benzyl-2-morpholinyl)-methyl]-2-butoxy-5-chlorobenzamide fumarate hemihydrate | 10 g |
| Corn starch | 220 g |
| Lactose | 730 g |
| Hydroxypropylcellulose | 30 g |
| Light anhydrous silicic acid | 10 g |

The above components are blended and made into fine granules by a conventional method.

What is claimed is:

1. A compound of the formula:

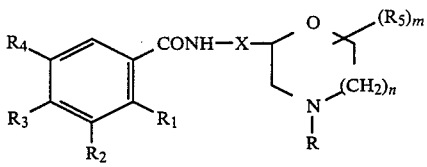

wherein R is —T—$R_6$ wherein T is a $C_1$-$C_6$ alkylene, and $R_6$ is phenyl or a phenyl substituted by one to five groups, each independently selected from the group consisting of a halogen, a $C_1$-$C_4$ alkyl, trifluoromethyl, a $C_1$-$C_4$ alkoxy, nitro, cyano and amino, $R_1$ is a halogen, hydroxy, a $C_1$-$C_{12}$ alkoxy, a $C_3$-$C_6$ cycloalkyloxy, a $C_3$-$C_8$ alkenyloxy, a $C_3$-$C_8$ alkynyloxy, a $C_2$-$C_6$ alkoxy interrupted by one or two oxygens or carbonyls, a $C_1$-$C_4$ alkylthio, amino, a monosubstituted amino in which the substituent is a $C_1$-$C_8$ alkyl, a phenyl($C_1$-$C_3$) alkyl or a $C_3$-$C_6$ cycloalkyl, a $C_2$-$C_6$ alkoxy in which the carbon atom at any position other than the 1-position is substituted by one hydroxy or amino, or a substituted $C_1$-$C_6$ alkoxy in which the substituent is a halogen, cyano, a $C_2$-$C_5$ alkoxycarbonyl, phthalimido, a $C_3$-$C_6$ cycloalkyl, a phenyl optionally substituted by one halogen, a phenoxy optionally substituted by one halogen, or a benzoyl optionally substituted by one halogen, $R_2$ is hydrogen, $R_3$ is hydrogen, a halogen, amino, a $C_1$-$C_4$ alkylamino, a di($C_1$-$C_4$ alkyl)amino, a $C_2$-$C_5$ alkanoylamino, or nitro, $R_4$ is hydrogen, a halogen, nitro, sulfamoyl, a $C_1$-$C_4$ alkylsulfamoyl, or a di($C_1$-$C_4$ alkyl)sulfamoyl, or any two adjacent groups of the $R_1$, $R_2$, $R_3$, and $R_4$ combine to form a $C_1$-$C_3$ alkylenedioxy, and the remaining two groups are each hydrogen, $R_5$ is hydrogen or a $C_1$-$C_4$ alkyl, X is a $C_1$-$C_3$ alkylene, m is 1 or 2, and n is 1, provided that at least one of the groups $R_2$, $R_3$ and $R_4$ is not hydrogen, or a pharmaceuticlly acceptable acid addition salt, quaternary ammonium salt, or N-oxide derivative thereof.

2. The compound according to claim 1, wherein R is

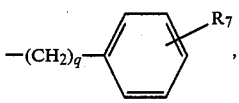

pentafluorobenzyl, 2-nitro-4-chlorobenzyl, or 1-phenylethyl; $R_1$ is hydroxy, a $C_1$-$C_{10}$ alkoxy, a $C_5$-$C_6$ cycloalkyloxy, a $C_3$-$C_5$ alkenyloxy, a $C_3$-$C_5$ alkynyloxy, a $C_2$-$C_4$ alkoxy interrupted by one carbonyl, a $C_2$-$C_5$ alkoxy in which the carbon atom at any position other than the 1-position is substituted by one hydroxy, or a substituted $C_1$-$C_5$ alkoxy in which the substituent is a halogen, cyano, a $C_2$-$C_4$ alkoxycarbonyl, a $C_3$-$C_5$ cycloalkyl, a phenyl optionally substituted by one halogen, a phenoxy optionally substituted by one halogen, or a benzoyl optionally substituted by one halogen, $R_2$ is hydrogen; $R_3$ is amino, a di($C_1$-$C_2$ alkyl)amino or a $C_2$-$C_5$ alkanoylamino; $R_4$ is chlorine; $R_5$ is hydrogen or methyl; $R_7$ is hydrogen, fluorine, chlorine, trifluoromethyl, cyano or nitro, X is methylene or ethylene; m is 1; and n is 1, q is an integer ranging from 1-4 or a pharmaceutically acceptable acid addition salt, quaternary ammonium salt, or N-oxide derivative thereof.

3. The compound according to claim 1 which has the formula:

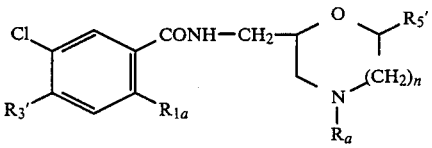

wherein $R_a$ is benzyl, fluorobenzyl, chlorobenzyl, trifluoromethylbenzyl, or cyanobenzyl, $R_{1a}$ is a $C_1$-$C_7$ alkoxy, cyclopentyloxy, 3-butenyloxy, 3-methyl-2-butenyloxy, 2-oxopropoxy, 2-hydroxypropoxy, or 2-chloroethoxy, $R_3'$ is amino, dimethylamino or a $C_2$–$C_3$ alkanoylamino,
$R_5$ is hydrogen or methyl, and
n is 1,
or a pharmaceutically acceptable acid addition salt, quaternary ammonium salt, or N-oxide derivative thereof.

4. The compound according to claim 3, wherein $R_3'$ is amino, or a pharmaceutically accepable acid addition salt, quaternary ammonium salt, or N-oxide derivative thereof.

5. The compound according to claim 4, wherein $R_a$ is 4-cyanobenzyl, $R_{1a}$ is methoxy and $R_5'$ is hydrogen, or a pharmaceutically acceptable acid addition salt thereof.

6. A compound of the formula:

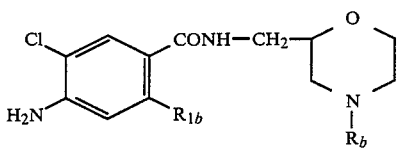

wherein $R_b$ is benzyl, fluorobenzyl, or chlorobenzyl, and
$R_{1b}$ is methoxy, ethoxy, butoxy, isobutoxy, pentyloxy, isopentyloxy, 3-methyl-2-butenyloxy, or 2-hydroxypropoxy,
or a pharmaceutically acceptable acid addition salt or N-oxide derivative thereof.

7. The compound according to claim 6, which is 4-amino-N-[(4-benzyl-2-morpholinyl)methyl]-2-butoxy-5-chlorobenzamide, or a pharmaceutically acceptable acid addition salt thereof.

8. The compound according to claim 6, which is 4-amino-2-butoxy-5-chloro-N-[[4-(4-fluorobenzyl)-2-morpholinyl]methyl]benzamide, or a pharmaceutically acceptable acid addition salt thereof.

9. The compound according to claim 6, which is 4-amino-N-[(4-benzyl-2-morpholinyl)methyl]-5-chloro-2-(3-methyl-2-butenyloxy)benzamide, or a pharmaceutically acceptable acid addition salt thereof.

10. The compound according to claim 6, which is 4-amino-N-[(4-benzyl-2-morpholinyl)methyl]-5-chloro-2-isopentyloxybenzamide, or a pharmaceutically acceptable acid addition salt thereof.

11. The compound according to claim 6, which is 4-amino-5-chloro-N-[[4-(2-chlorobenzyl)-2-morpholinyl]methyl]-2-ethoxybenzamide, or a pharmaceutically accetpable acid addition salt thereof.

12. The compound according to claim 6, which is 4-amino-N-[(4-benzyl-2-morpholinyl)methyl]-5-chloro-2-ethoxybenzamide, or a pharmaceutically acceptable acid addition salt thereof.

13. The compound according to claim 6, which is 4-amino-N-[(4-benzyl-2-morpholinyl)methyl]-5-chloro-2-methoxybenzamide, or a pharmaceutically acceptable acid addition salt thereof.

14. 4-Amino-5-chloro-2-ethoxy-N-[[4-(4-fluorobenzyl)-2-morpholinyl]methyl]benzamide or a pharmaceutically acceptable acid addition salt thereof.

15. A pharmaceutical composition comprising an effective amount of a compound as set forth in claim 1, or a pharmaceutically acceptable acid addition salt, quaternary ammonium salt, or N-oxide derivative thereof in admixture with a pharmaceutically acceptable carrier or diluent.

16. A pharmaceutical composition comprising an effective amount of a compound as set forth in claim 2, or a pharmaceutically acceptable acid addition salt, quaternary ammonium salt, or N-oxide derivative thereof in admixture with a pharmaceutically acceptable carrier or diluent.

17. A pharmaceutical composition comprising an effective amount of a compound as set forth in claim 3, or a pharmaceutically acceptable acid addition salt, quaternary ammonium salt, or N-oxide derivative thereof in admixture with a pharmaceutically acceptable carrier or diluent.

18. A pharmaceutical composition comprising an effective amount of a compound as set forth in claim 4, or a pharmaceutically acceptable acid addition salt, quaternary ammonium salt, or N-oxide derivative thereof in admixture with a pharmaceutically acceptable carrier or diluent.

19. A pharmaceutical composition comprising an effective amount of a compound as set forth in claim 5, or a pharmaceutically acceptable acid addition salt thereof in admixture with a pharmaceutically acceptable carrier or diluent.

20. A pharmaceutical composition comprising an effective amount of a compound as set forth in claim 6, or a pharmaceutically acceptable acid addition salt or N-oxide derivative thereof in admixture with a pharmaceutically acceptable carrier or diluent.

21. A pharmaceutical composition comprising an effective amount of a compound as set forth in claim 7, or a pharmaceutically acceptable acid addition salt thereof in admixture with a pharmaceutically acceptable carrier or diluent.

22. A pharmaceutical composition comprising an effective amount of a compound as set forth in claim 8, or a pharmaceutically acceptable acid addition salt thereof in admixture with a pharmaceutically acceptable carrier or diluent.

23. A pharmaceutical composition comprising an effective amount of a compound as set forth in claim 9, or a pharmaceutically acceptable acid addition salt thereof in admixture with a pharmaceutically acceptable carrier or diluent.

24. A pharmaceutical composition comprising an effective amount of a compound as set forth in claim 10, or a pharmaceutically acceptable acid addition salt thereof in admixture with a pharmaceutically acceptable carrier or diluent.

25. A pharmaceutical composition comprising an effective amount of a compound as set forth in claim 11, or a pharmaceutically acceptable acid addition salt thereof in admixture with a pharmaceutically acceptable carrier or diluent.

26. A pharmaceutical composition comprising an effective amount of a compound as set forth in claim 12, or a pharmaceutically acceptable acid addition salt thereof in admixture with a pharmaceutically acceptable carrier or diluent.

27. A pharmaceutical composition comprising an effective amount of a compound as set forth in claim 13, or a pharmaceutically acceptable acid addition salt thereof in admixture with a pharmaceutically acceptable carrier or diluent.

28. A pharmaceutical composition comprising an effective amount of a compound as set forth in claim 14, or a pharmaceutically acceptable acid addition salt thereof in admixture with a pharmaceutically acceptable carrier or diluent.

* * * * *

UNITED STATES PATENT AND TRADEMARK OFFICE
CERTIFICATE OF CORRECTION

PATENT NO. : 4,870,074
DATED : September 26, 1989
INVENTOR(S) : Tatsuya Kon, et al.

It is certified that error appears in the above-identified patent and that said Letters Patent is hereby corrected as shown below:

Column 1, Line 14, "(1970)" should read as --(1979)--.

Column 2, Line 15, "substituted" should read as --substituent--.

Column 4, delete Lines 10-25 and substitute therefor,

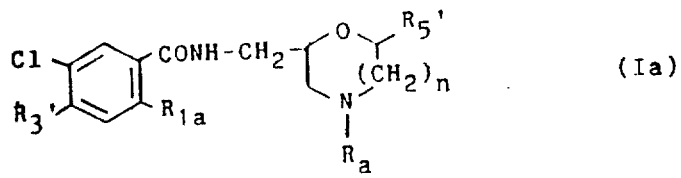

Column 5, Line 43, "group" (sec. occur.) should read as --product--.

Column 6, Line 8, "12,3-benzotriazine" should read as --1,2,3-benzotriazine--.

Column 10, Line 7, "of" should read as --or--.

Column 12, Line 19, "222-227" should read as --222-257--.

Column 18, Line 27, "hexanechloroform" should read as --hexane-chloroform--.

Column 20, Line 40, "difurmate" should read as --difumarate--.

Column 22, Line 17, under previous " " ", insert --"--.

UNITED STATES PATENT AND TRADEMARK OFFICE
CERTIFICATE OF CORRECTION

PATENT NO. : 4,870,074
DATED : September 26, 1989
INVENTOR(S) : Tatsuya Kon, et al.

It is certified that error appears in the above-identified patent and that said Letters Patent is hereby corrected as shown below:

Column 23, Line 22, "$CH_3$" should read as --$CH_2$--.

Column 25, Line 47, "$(CH_2)_3F$" should read as --$(CH_2)_3S$--.

Columns 29-30, Line 65, text is misaligned.

Column 35, Line 62, after "is" insert --added--.

Column 36, Line 34, "(1(1)" should read as --1(1)--.

Column 36, Line 66, after "as" insert --in--.

Column 38, Line 21, "coolinga" should read as --cooling a--.

Column 46, Line 2, "morphoine" should read as --morpholine--.

Column 51, Line 61, "-acetylamino" should read as --2-acetylamino--.

UNITED STATES PATENT AND TRADEMARK OFFICE
CERTIFICATE OF CORRECTION

PATENT NO. : 4,870,074

DATED : September 26, 1989

INVENTOR(S) : Tatsuya Kon, et al.

It is certified that error appears in the above-identified patent and that said Letters Patent is hereby corrected as shown below:

Column 55, line 51: "accetpable" should read as --acceptable--

Signed and Sealed this

Thirty-first Day of December, 1991

Attest:

HARRY F. MANBECK, JR.

Attesting Officer Commissioner of Patents and Trademarks